US007670782B2

(12) United States Patent
Zerangue

(10) Patent No.: US 7,670,782 B2
(45) Date of Patent: Mar. 2, 2010

(54) SCREENING OF COMPOUNDS FOR CAT1 TRANSPORTER ACTIVITY

(75) Inventor: Noa Zerangue, Sunnyvale, CA (US)

(73) Assignee: XenoPort, Inc., Santa Clara, CA (US)

( * ) Notice: Subject to any disclaimer, the term of this patent is extended or adjusted under 35 U.S.C. 154(b) by 298 days.

(21) Appl. No.: 11/493,363

(22) Filed: Jul. 25, 2006

(65) Prior Publication Data
US 2007/0054324 A1 Mar. 8, 2007

Related U.S. Application Data

(60) Provisional application No. 60/703,571, filed on Jul. 29, 2005.

(51) Int. Cl.
*G01N 33/53* (2006.01)
*G01N 33/557* (2006.01)
*G01N 33/566* (2006.01)
(52) U.S. Cl. ...................................................... 435/7.1
(58) Field of Classification Search ....................... None
See application file for complete search history.

(56) References Cited

U.S. PATENT DOCUMENTS

| | | | |
|---|---|---|---|
| 6,187,566 B1 * | 2/2001 | Dattagupta et al. | 435/91.1 |
| 6,361,938 B1 * | 3/2002 | O'Mahony et al. | 435/6 |
| 6,395,960 B1 * | 5/2002 | St. George-Hyslop et al. | 800/18 |
| 6,489,302 B1 | 12/2002 | Wiessler et al. | |
| 2002/0019019 A1 * | 2/2002 | Hamalainen et al. | 435/7.92 |
| 2002/0045254 A1 | 4/2002 | Hosoya et al. | |
| 2005/0123982 A1 | 6/2005 | Zhu et al. | |

FOREIGN PATENT DOCUMENTS

EP 0959136 A1 11/1999

OTHER PUBLICATIONS

Stoll 1993 (Journal of Neurochemistry 60:1956-1959).*
GenBank accession L10152 (see printout dated Dec. 5, 2008).*
Mann 2003 (Physiol Rev 83:183-252).*
Umeki 2002 (Drug Metabol. Pharmacokin 17:367-373).*
Smith 1987 (Journal of Neurochemistry 49:1651-1658).*
Kavanaugh 1993 (Biochemistry 32:5781-5785).*
Soares-Da-Silva 2000 (Am J Physiol Renal Physiol 279:F736-F746).*
Hoyosa (2000. AAPS Pharmsci 2(3); article 27, pp. 1-11).*
Takada (1992. Cancer Research 52:2191-2196).*
Pardridge (1990. Journal of Pharmacology and Experimental Therapeutics 255:893-899).*
Rotmann 2004 (Biochimica et Biophysica Acta 1660:138-143).*
Gengo (1996. J Allergy Clin Immunol 98:S319-S325).*
Mackic (1999. Pharm Res 16:1360-1365).*
Lee 2002 (Journal of Nuclear Medicine 43:948-956).*
Batrakova, E.V. et al.; "Pluronic P85 enhances the delivery of digoxin to the brain: in virto and in vivo studies"; 2001, *The Journal of Pharmacology and Experimental Therapeutics*, vol. 296, No. 2, pp. 551-557, 1 page abstract only.

Pardridge, William M.; "Blood-Brain Barrier Drug Targeting: The Future of Brain Drug Development"; 2003, *Molecular Interventions*, vol. 3, No. 2, pp. 90-105.
Tsuji, Akira; "Small Molecular Drug Transfer across the Blood-Brain Barrier via Carrier-Mediated Transport Systems"; 2005, *The Journal of the American Society for Experimental NeuroTherapeutics*, vol. 2, pp. 54-62.
Alderman, D.A., "A review of cellulose ethers in hydrophilic matricies for oral controlled-release dosage forms," *Int. J. Pharm. Tech. & Prod. Mfr.*, 5(3):1-9 (1984).
Altschul et al., "Basic Local Alignment Search tool," *J. Mol. Biol.*, 215:403-410 (1990).
Audus et al., "The use of cultured epithelial and endothelial cells for drug transport and metabolism studies," *Pharm. Res.*, 7:435-451 (1990).
Audus et al., "Characterization of an in viro blood-brain barrier model system for studyong drug transport and metabolism," *Pharm, Res.*, 3:81-87 (1986).
Bamba et al., "Release mechanisms in gelforming sustained release preparations," *Int. J. Pharm.*, 2:307-305 (1979).
Bowman et al., "Brain microvessel endothelial cells in tissue culture: A model for study of blood-barrier permeability," *Ann. Neurol.*, 14:396-402 (1983).
*Controlled Drug Biovavailbilty*, vol. 1, *Drug Product Design and Performance*, Smolen and Ball (eds.), Wiley, New York (1984), Table of contents only.
Cserr et al., "Blood-brain interfaces in verbrates: a comparative approach," *Am. J. Physiol. Regul. Integr. Comp. physiol.*, 246,R277-R288 (1984).
During et al., "Controlled Release of Dopamine from a Polymeric Brain Implant: In Vivo Characterization," 1989, *Ann. Neurol*, 25:351-356 (1989).
Goldstein et al. "The Blood-Brain Barrier," *Scientific American*, 255:74-83 (1986).
Hanes et al., "New Advances in Microphere-based single-dose vaccines," *Advances Drug Delivery Reviews*, 28:97-119 (1997).
Henikoff et al., "Amino acid substitution matricies from protein blocks," *PNAS*, 89:10915-10919 (1989).
Howard et al., "Intracerebral drug delivery in rats with lesion-induced memory deficits," *J. Neurosurg.*, 71:105-112 (1989).
Karlin et al., "Applications and statics for multiple high -scoring segments in molecular sequences," *PNAS*, 90:5873-5787 (1993).
Langer et al., "Chemical and Physical Structure of Polymers as Carriers for Contriolled Release of Bioactive Agents: A Review," *JMS-REV. Macromol. Chem. Phys.*, C23(1):61-126 (1983).
Langer, R., "New Methods of Drug Delivery," *Science*, 249:1527-1533 (1990).
Levy et al., "Inhibition of Calcification of Bioprosthetic Heart valves by Local Controlled-Release Diphosphonate," *Science*, 228:190-192 (1985).

(Continued)

*Primary Examiner*—Daniel E. Kolker
(74) *Attorney, Agent, or Firm*—D. Byron Miller; William R. Lambert; Lucy S. Chang

(57) ABSTRACT

CAT1 is consistently expressed at high levels in brain microvessel endothelial cells. Disclosed herein are assays for determining whether a test material/molecule is a substrate for, and/or is actively transported by, the CAT1 transporter, and therefore a candidate substrate for crossing the blood brain barrier. The assays are useful in screening for therapeutic, cytotoxic or imaging compounds used in the treatment or diagnosis of neurological diseases.

8 Claims, 3 Drawing Sheets

OTHER PUBLICATIONS

Masereeuw et al., "In vitro and in vivo transport of zidovudine (AZT) across the blood-brain barrier and the effect of transport inhibitors," *Pharm. Res.*, 11(2):324-330 (1994).

*Medical Applications of Controlled Release,* Langer and Wise (eds.), cover page and table of contents, CRCPres., Boca Raton, Florida (1974).

Meresse et al., "Bovine brain endothelial cells express tight junctions and monoamine oxidase acitivty in long-term culture," *J. Neurochem.*, 53:1363-1371 (1989).

Needleman et al., "A General Method Applicable to the Search for Similarities in the Amino Acid Sequence of Two Proteins," *J. Mol. Biol.*, 48:443-453 (1970).

Neuwelt, eds., *Implications of the blood-brain barrier and its manipulation,* vol. 1 *Basic Science Aspects,* Plenum Medical, New York (1989), Table of contents for vol. 1.

Pardridge, W.M., "Receptor-Mediated Peptide Transport through the Blood-Brain Barrier," *Endocrin. Rev.*, 7(3):314-330 (1986).

Pardridge et al., "Comparison of in vitro and in vivo models of drug transcytosis through the blood-brain barrier," *J. Pharmacol. Exp. Thera.*, 253(2):884-891 (1990).

Pearson et al., "Improved tools for biological sequence comparison," *PNAS*, 85:24442448 (1988).

Remington's Pharmaceutical Sciences, Mace Publishing Company, Philadelphia, PA, 17th ed. (1985), p. xvi only.

Smith et al., "Comparison of Biosequences," *Adv. Appl. Math.*, 2:482-489 (1981).

Terasaki et al., "New approaches to in vitro moidels of blood-brain barrier drug transport," *Drug Discovery Today*, 8(20):944-954 (2003).

Tietz et al., "Fluorokinase abd Pyruvic Kinase," *Arch. Biochim. Biophys.*, 78:477-493 (1958).

* cited by examiner

CAT1 SUBSTRATES

A.

B.

C.

SCREENING OF COMPOUNDS FOR CAT1 TRANSPORTER ACTIVITY

This application claims benefit of U.S. Provisional Application No. 60/703,571 filed Jul. 29, 2005, which is incorporated by reference herein in its entirety.

TECHNICAL FIELD

The disclosures herein relate to assays and methods of using the same for screening compounds and/or chemical moieties for their ability to be actively transported across the blood brain barrier.

BACKGROUND

The capillaries that supply blood to the tissues of the brain constitute the blood brain barrier (Goldstein et al. (1986) Scientific American 255:74-83; Pardridge, W. M. (1986) Endocrin. Rev. 7:314-330). The endothelial cells, which form the brain capillaries, are different from those found in other tissues in the body. Brain capillary endothelial cells are joined together by tight intercellular junctions, which form a continuous wall against the passive diffusion of molecules from the blood to the brain and other parts of the central nervous system (CNS). These cells are also different in that they have few pinocytic vesicles, which in other tissues allow somewhat unselective transport across the capillary wall. Also lacking are continuous gaps or channels running between the cells that would allow unrestricted passage.

The blood-brain barrier functions to ensure that the environment of the brain is constantly controlled. The levels of various substances in the blood, such as hormones, amino acids and ions, undergo frequent small fluctuations, which can be brought about by activities such as eating and exercise (Goldstein et al., cited supra). If the blood brain barrier did not protect the brain from these variations in serum composition, the result could be uncontrolled neural activity.

The isolation of the brain from the bloodstream is not complete. If this were the case, the brain would be unable to function properly due to a lack of nutrients and because of the need to exchange chemicals with the rest of the body. The presence of specific transport systems within the capillary endothelial cells assures that the brain receives, in a controlled manner, all of the compounds required for normal growth and function. In many instances, these transport systems consist of membrane-associated proteins, which selectively bind and transport certain molecules across the barrier membranes. These transporter proteins are known as solute carrier transporters.

The problem posed by the blood brain barrier is that, in the process of protecting the brain, it excludes many potentially useful therapeutic agents. Presently, only substances that are sufficiently lipophilic can penetrate the blood-brain barrier (Goldstein et al., cited supra; Pardridge, W. M., cited supra). Some drugs can be modified to make them more lipophilic and thereby increase their ability to cross the blood brain barrier. However, each modification must be tested individually on each drug and the modification can alter the activity of the drug.

Because the blood brain barrier is composed of brain microvessel endothelial cells, these cells have been isolated and cultured for use in in vitro model systems for studying the blood brain barrier (Bowman et al., Brain microvessel endothelial cells in tissue culture: A model for study of blood-brain barrier permeability, Ann. Neurol. 14, 396-402 (1983); Audus and Borchardt, Characterization of an in vitro blood-brain barrier model system for studying drug transport and metabolism, Pharm, Res. 3, 81-87 (1986)). In vitro model systems of the blood brain barrier have been successfully derived from bovine, canine, human, murine, porcine, and rat cells, and have similar permeability properties due to similarity of the physiological characteristics of the blood brain barrier among mammals (Cserr et al., Blood-brain interfaces in vertebrates: a comparative approach, Am. J. Physiol. 246, R277-R288 (1984); Audus et al., The use of cultured epithelial and endothelial cells for drug transport and metabolism studies, Pharm. Res. 7, 435-451 (1990)). In these models, the cultured endothelial cells retain the characteristics of brain endothelial cells in vivo, such as morphology, specific blood brain barrier enzyme markers, and tight intercellular junctions. The cells can also be used for the study of passive diffusion, carrier mediated transport, and metabolism to specific factors affecting the blood brain barrier permeability. However, passaging of brain microvessel endothelial cells results in loss of specific endothelial and blood brain barrier markers as well as tight intercellular junctions (Brightman and Neuwelt (ed.), Implications of the blood-brain barrier and its manipulation, Vol. 1, Plenum Medical, New York, pp. 53-83 (1989)).

Currently, primary cultures of brain microvessel endothelial cells are the principal tool for in vitro prediction of blood brain barrier permeability. Isolated and cultured primary brain cells developed previously have exhibited different properties primarily due to considerable variability in the starting material. For example, with respect to transcellular transport, rigorous comparison of data between different laboratories has been very difficult (Pardridge et al., Comparison of in vitro and in vivo models of drug transcytosis through the blood-brain barrier, J. Pharmacol. Exp. Thera. 253, 884-891 (1990); Masereeuw et al., In vitro and in vivo transport of zidovudine (AZT) across the blood-brain barrier and the effect of transport inhibitors, Pharm. Res., 11, 324-330 (1994)). Passaging primary cells can affect the differentiation of cells and lead to the selection of the most rapidly proliferating clones. Furthermore, the expression of some marker enzymes such as gamma-glutamyl transpeptidase as well as tight junctional complexity has been shown to decrease with time in culture and passage number (Meresse et. al., Bovine brain endothelial cells express tight junctions and monoamine oxidase activity in long-term culture, J. Neuorchem. 53, 1363-1371 (1989)). Some transporter substrates have been demonstrated to accumulate in the brain (see U.S. Pat. No. 6,489,302).

Thus, it is apparent that the presently available clones of immortalized brain microvessel endothelial cell cultures suffer from individual drawbacks in terms of phenotype expression and homogeneic maintenance of that expression. This leads to difficulties with respect to accuracy and reproducibility in studies utilizing brain microvessel endothelial cells to model passage of chemical compounds and moieties, e.g., potential therapeutic compounds and/or drug moieties, across the blood brain barrier.

SUMMARY

Disclosed herein are methods of screening agents, conjugates or conjugate moieties for the ability to enter the CNS by crossing the blood brain barrier in order to treat or diagnose conditions within the CNS. These methods entail providing a cell expressing the CAT1 transporter, the transporter being situated in the plasma membrane of the cell. The cell is contacted with an agent, conjugate, or conjugate moiety. Whether the agent, conjugate, or conjugate moiety passes through the plasma membrane via the CAT1 transporter is determined. If the method comprises contacting the cell with an agent, the agent is a neuropharmaceutical agent or an imaging component. If the method comprises contacting the cell with a conjugate, the conjugate comprises an agent that is a neuropharmaceutical agent or an imaging component. If the method comprises contacting the cells with a conjugate moiety, the method further comprises linking the conjugate moiety to an agent that is a neuropharmaceutical agent or an imaging component.

In some methods, the cell endogenously expresses the CAT1 transporter. In other methods a nucleic acid molecule encoding the CAT1 transporter has been transfected or injected into the cell. In some methods the cell is a brain microvessel endothelial cell. In other methods the cell is an oocyte. In other methods the cell is a human embryonic kidney (HEK) cell. In other methods the cell is a Madin Darby canine kidney (MDCK) cell. In other methods the cell is a porcine kidney epithelial (LLCPK) cell. In other methods the cell is a Chinese hamster ovary (CHO) cell. In still other methods, the cell is constructed to conditionally express the transporter.

In some methods the agent, conjugate, or conjugate moiety comprises an amino acid. In some methods the agent, conjugate, or conjugate moiety is administered to an undiseased animal and any toxic effects are determined. In some methods the neuropharmaceutical agent is a cytotoxic neuropharmaceutical agent selected from the group consisting of platinum, nitrosourea, a phosphoramide group that is selectively cytotoxic to brain tumor cells, nitroimidazole, and nitrogen mustard.

Disclosed herein are methods of screening agents, conjugates or conjugate moieties for the ability to enter the CNS by crossing the blood brain barrier wherein a cell used for testing is a brain microvessel endothelial cell that is one of a plurality of brain microvessel endothelial cells forming a polarized monolayer. An agent, conjugate, or conjugate moiety is contacted to one side of the polarized monolayer and whether the agent, conjugate, or conjugate moiety is transported into the brain microvessel endothelial cells or to the opposite side of the polarized monolayer is determined. Some methods further comprise administering the agent, conjugate, or conjugate moiety to a peripheral tissue of an animal and measuring the amount of agent, conjugate, or conjugate moiety that passes through the blood brain barrier into the brain of the animal.

Disclosed herein are methods of screening an agent, conjugate, or conjugate moiety for neuropharmacological activity useful for treating neurological disorders. In these methods, one determines whether the agent, conjugate, or conjugate moiety is transported through the CAT1 transporter. One then administers the agent, conjugate, or conjugate moiety to a test animal and determines whether the agent, conjugate, or conjugate moiety is actively transported across the blood brain barrier by measuring agent, conjugate, or conjugate moiety concentrations found in the CNS of the animal. For those agents, conjugates or conjugate moieties that are transported in sufficient quantities, the agents, conjugates, or conjugate moieties can be further tested in animals suffering from a particular neurological disorder to determine whether the agents, conjugates or conjugate moieties have the requisite therapeutic neuropharmacological activity for treating such neurological disorder.

Also disclosed herein are methods for in vitro screening of agents, conjugates or conjugate moieties for improved retention in the CNS. In these methods, one determines the substrate properties of a compound on both uptake transporters and efflux transporters. An agent, conjugate, or conjugate moiety is first tested for activity on the CAT1 transporter. The agent, conjugate, or conjugate moiety is then tested for substrate activity on an efflux transporter, such as P Glycoprotein (PgP). Those agents, conjugates or conjugate moieties active on both the efflux transporter and CAT1 are then modified and tested for a reduction of efflux substrate activity and retested for retention of activity on the CAT1 transporter. This iterative process produces an agent, conjugate, or conjugate moiety with an increased ratio of substrate activities in the uptake and efflux systems, and improved retention of pharmacological levels of the modified agent, conjugate, or conjugate moiety in the CNS.

Disclosed herein are methods of screening an agent, conjugate, or conjugate moiety for capacity to be transported into the brain, comprising determining whether the agent, conjugate, or conjugate moiety specifically binds to a CAT1 transporter, contacting the agent to one side of a polarized monolayer of cells, and determining whether the agent is actively transported across the polarized monolayer. In some methods the specific binding is determined by contacting a cell expressing the CAT1 transporter, the transporter being situated in the plasma membrane of the cell, with a substrate of the CAT1 transporter, and determining whether the agent inhibits transport of the substrate across the polarized monolayer.

Disclosed herein are pharmaceutical compositions comprising a therapeutic neuropharmaceutical agent, a cytotoxic neuropharmaceutical agent or an imaging component linked to a conjugate moiety to form a conjugate in which the conjugate moiety has a higher $V_{max}$ for the CAT1 transporter than the therapeutic neuropharmaceutical agent, cytotoxic neuropharmaceutical agent or imaging component alone. Some pharmaceutical compositions have at least 5 times the $V_{max}$ for CAT1 than the neuropharmaceutical agent or the imaging component alone. In some pharmaceutical compositions the conjugate has a $V_{max}$ for CAT1 that is at least 5% of the $V_{max}$ for CAT1 of a compound selected from the group comprising arginine, lysine, ornithine, N-methyl arginine, and dimethyl arginine. In some pharmaceutical compositions the conjugate has a lower $V_{max}$ for an efflux transporter than the neuropharmaceutical agent or the imaging component alone.

Disclosed herein are methods of formulating a therapeutic neuropharmaceutical agent, a cytotoxic neuropharmaceutical agent or an imaging component. These methods entail linking the therapeutic neuropharmaceutical agent, the cytotoxic neuropharmaceutical agent or the imaging component to a conjugate moiety to form a conjugate, wherein the conjugate moiety has a greater $V_{max}$ for the CAT1 transporter than the therapeutic neuropharmaceutical agent, the cytotoxic neuropharmaceutical agent or the imaging component alone. The conjugate is formulated with a pharmaceutical carrier as a pharmaceutical composition.

Disclosed herein are methods of delivering a therapeutic neuropharmaceutical agent, a cytotoxic neuropharmaceutical agent or an imaging component. The methods involve administering to a patient a pharmaceutical composition comprising a therapeutic neuropharmaceutical agent, a cytotoxic neuropharmaceutical agent or an imaging component linked to a conjugate moiety to form a conjugate, wherein the conjugate has a higher $V_{max}$ for the CAT1 transporter than the therapeutic neuropharmaceutical agent, cytotoxic neuropharmaceutical agent or imaging component alone, whereby the conjugate passes through brain microvessel endothelial cells which make up the blood brain barrier, via the CAT1 transporter, into the CNS of the patient. Also disclosed herein are methods of delivering a conjugate, comprising administering to a patient a pharmaceutical composition comprising a neuropharmaceutical agent or imaging component linked to a conjugate moiety to form the conjugate, wherein the conjugate has a higher $V_{max}$ for the CAT1 transporter than the neuropharmaceutical agent or imaging component alone. In some methods the $V_{max}$ of the conjugate is at least two-fold higher than that of the neuropharmaceutical agent or imaging component alone. In some methods the neuropharmaceutical agent is a cytotoxic neuropharmaceutical selected from the group consisting of platinum, nitrosourea, a phosphoramide group selectively cytotoxic to brain tumor cells, nitroimidazole, and nitrogen mustard.

Disclosed herein are methods of treating neurological disorders. These methods entail administering to a patient an effective amount of an agent that is transported by CAT1, wherein the agent is a conjugate comprising a therapeutic neuropharmaceutical agent, a cytotoxic neuropharmaceutical agent or an imaging component linked to a conjugate moiety.

Disclosed herein are methods of screening an agent for decreased side effects in the central nervous system (CNS), comprising providing an agent having a pharmacological activity, wherein the pharmacological activity is useful for treating a disease present in a tissue other than the CNS, and the pharmacological activity results in undesired side effects in the CNS if the agent enters the CNS, modifying the agent, providing a cell expressing at least one efflux transporter protein that transports substrates out of the CNS, contacting the cell with the modified agent, and determining whether the modified agent is transported by the at least one efflux transporter protein with a higher $V_{max}$ than the agent, a higher $V_{max}$ indicating that the modification increases the capacity of the modified agent relative to the agent to be transported out of the CNS, thereby decreasing undesired side effects in the CNS.

DEFINITIONS

Figure 1:
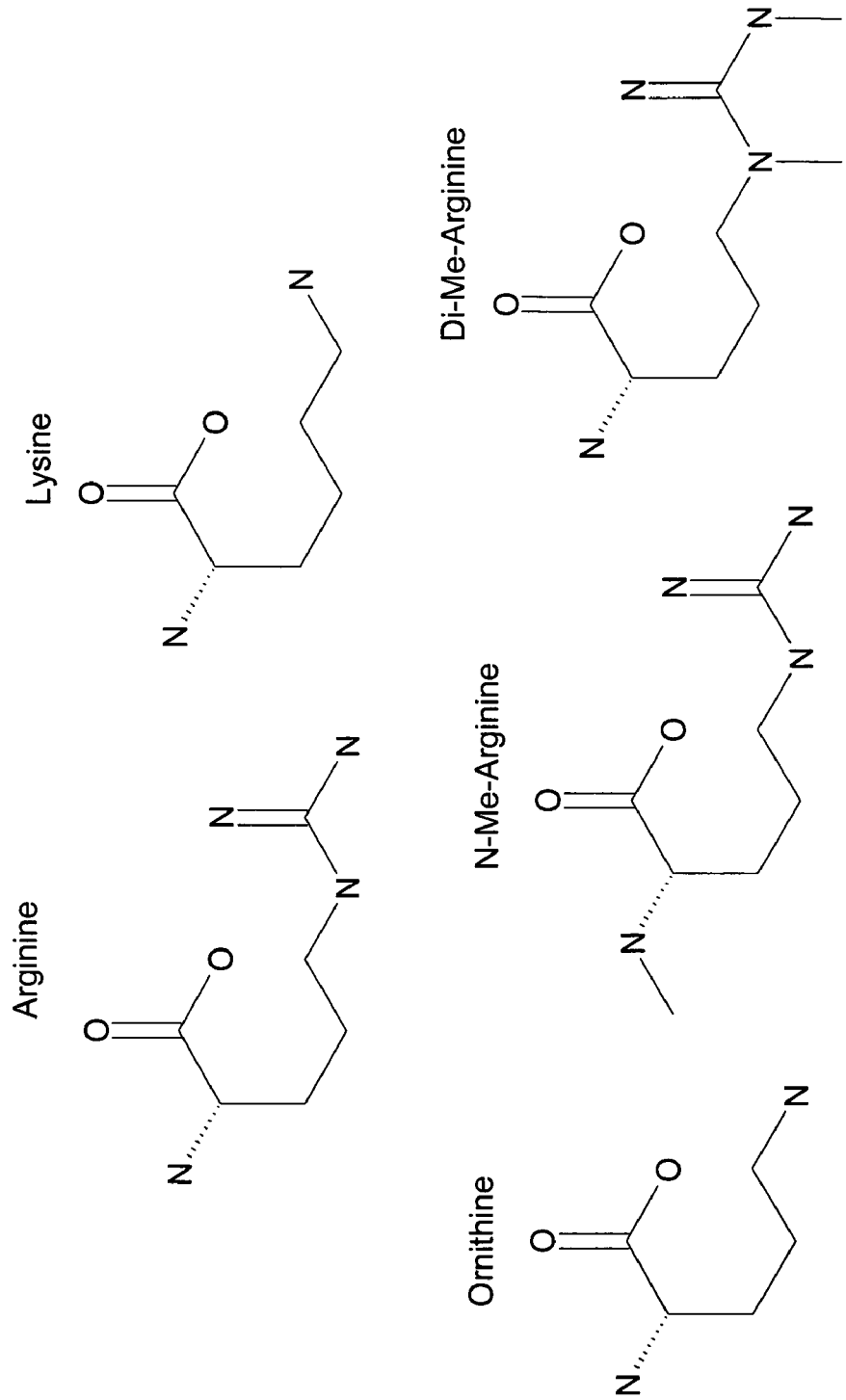
FIG. 1 shows the structures of known substrates of the CAT1 transporter.

"Transport by passive diffusion" refers to transport of an agent that is not mediated by a specific transporter protein. An agent that is substantially incapable of passive diffusion has a permeability across a standard cell monolayer (e.g., Caco-2 or MDCK cells or an artificial bilayer (PAMPA)) of less than $5\times10^{-6}$ cm/sec, and usually less than $1\times10^{-6}$ cm/sec in the absence of an efflux mechanism.

A "substrate" of a transporter protein is a compound whose uptake into or passage through the plasma membrane of a cell is facilitated at least in part by a transporter protein.

The term "ligand" of a transporter protein includes compounds that bind to the transporter protein. Some ligands are transported and are thereby also substrates. Some ligands inhibit or antagonize transport of a substrate by the transporter protein. Some ligands bind in a manner non-competitive with substrates and modulate the transport of substrates by the transporter protein.

The term "neuropharmaceutical agent" is used to describe a compound that has or may have a pharmacological activity in the treatment or prophylaxis of a neurological disorder. Neuropharmaceutical agents include compounds that are known drugs, compounds for which pharmacological activity has been identified but which are undergoing further therapeutic evaluation, and compounds that are members of collections and libraries that are to be screened for a pharmacological activity. The neuropharmaceutical agent can be a compound having a therapeutic, prophylactic or cytotoxic effect on a neurological disease including any condition that affects biological functioning of the central nervous system. Examples of neurological diseases include cancer (e.g., brain tumors), Acquired Immune Deficiency Syndrome (AIDS), stroke, epilepsy, Parkinson's disease, multiple sclerosis, neurodegenerative disease, trauma, depression, Alzheimer's disease, migraine, pain, or a seizure disorder. Classes of neuropharmaceutical agents include proteins, antibiotics, adrenergic agents, anticonvulsants, small molecules, nucleotide analogs, chemotherapeutic agents, anti-trauma agents, peptides and other classes of agents used in treatment or prophylaxis of a neurological disorder. Examples of such proteins include CD4 (including soluble portions thereof), growth factors (e.g., nerve growth factor and interferon), dopamine decarboxylase and tricosanthin. Examples of such antibiotics include amphotericin B, gentamycin sulfate, and pyrimethamine. Examples of such adrenergic agents (including blockers) include dopamine and atenolol. Examples of such chemotherapeutic agents include adriamycin, methotrexate, cyclophosphamide, etoposide, and carboplatin. An example of an anticonvulsant that can be used is valproate and an anti-trauma agent that can be used is superoxide dismutase. Examples of such peptides are somatostatin analogues and enkephalinase inhibitors. Nucleotide analogs that can be used include azido thymidine (hereinafter AZT), dideoxy Inosine (ddl), and dideoxy cytodine (ddc).

The term "agent" is used to describe a compound that has or may have a pharmacological activity. Agents include compounds that are known drugs, compounds for which pharmacological activity has been identified but which are undergoing further therapeutic evaluation, and compounds that are members of collections and libraries that are to be screened for a pharmacological activity.

A "pharmacological" activity means that an agent exhibits an activity in a screening system that indicates that the agent is or may be useful in the prophylaxis or treatment of a disease. The screening system can be in vitro, cellular, animal or human. Agents can be described as having pharmacological activity notwithstanding that further testing may be required to establish actual prophylactic or therapeutic utility in treatment of a disease.

An agent is "orally active" if it can exert a pharmacological activity when administered via an oral route.

A "peripheral tissue" means a tissue other than the CNS.

A "conjugate" refers to a compound comprising a neuropharmaceutical agent or imaging component and a chemical moiety bound thereto, which moiety by itself or in combination with the neuropharmaceutical agent or imaging component renders the conjugate a substrate for active transport, for example rendering the conjugate to be a substrate for a transporter protein. The chemical moiety may or may not be subject to cleavage from the neuropharmaceutical agent or imaging component upon uptake and metabolism of the conjugate in the patient's body. In other words, the moiety may be cleavably bound to the neuropharmaceutical agent or imaging component or non-cleavably bound to the neuropharmaceutical agent or imaging component. The bond can be a direct (i.e., covalent) bond or the bond can be through a linker. In cases where the bond/linker is cleavable by metabolic processes, the neuropharmaceutical agent or imaging component, or a further metabolite of the neuropharmaceutical agent or imaging component, is the therapeutic or imaging entity. In cases where the bond/linker is not cleavable by metabolic processes, the conjugate itself is the therapeutic or imaging entity. Most typically, the conjugate comprises a prodrug having a metabolically cleavable moiety, where the conjugate itself does not have pharmacological activity but the component to which the moiety is cleavably bound does have pharmacological activity. Typically, the moiety facilitates therapeutic use of the neuropharmaceutical agent or imaging component by promoting uptake of the conjugate via a transporter. Thus, for example, a conjugate comprising a neuropharmaceutical agent and a conjugate moiety may have a $V_{max}$ for a transporter that is at least 2, 5, 10, 20, 50 or 100-fold higher than that of the neuropharmaceutical agent or imaging component alone. A conjugate moiety can itself be a substrate for a transporter or can become a substrate when linked to the neuropharmaceutical agent or imaging component. Examples of preferred conjugate moieties are arginine, lysine, ornithine, N-methyl arginine and dimethyl arginine. Thus, a conjugate formed from a neuropharmaceutical agent or imaging component and a conjugate moiety can have higher CNS uptake activity than the neuropharmaceutical agent, the imaging component, or the conjugate moiety alone.

A "neuropharmacological" activity means that a neuropharmaceutical agent exhibits an activity in a screening system that indicates that the neuropharmaceutical agent is or may be useful in the prophylaxis or treatment of a neurological disease. The screening system can be in vitro, cellular, animal or human. Neuropharmaceutical agents can be described as having neuropharmacological activity notwithstanding that further testing may be required to establish actual prophylactic or therapeutic utility in treatment of a disease.

$V_{max}$ and $K_m$ of a compound for a transporter are defined in accordance with convention. $V_{max}$ is the number of molecules of compound transported per second at saturating concentration of the compound. $K_m$ is the concentration of the compound at which the compound is transported at half of $V_{max}$. When the goal is to transport an agent, conjugate, or conjugate moiety into the CNS, a high $V_{max}$ for an influx transporter such as CAT1 is generally desirable. Likewise for the same goal, a low value of $K_m$ is typically desirable for transport of a compound present at low blood concentrations. In some cases a high value of $K_m$ is acceptable for the transport of compounds present at high concentrations in the blood. For these reasons, the intrinsic capacity of a compound to be transported by a particular transporter is usually expressed as the ratio $V_{max}$ of the compound/$V_{max}$ of a reference compound known to be a substrate for the transporter. $V_{max}$ is affected both by the intrinsic turnover rate of a transporter (molecules/transporter protein) and transporter density in the plasma membrane, which depends on expression level. In certain instances, the goal is to avoid transport into the CNS. In these instances, a low $V_{max}$ for all influx transporters and a high $V_{max}$ for all efflux transporters expressed in the blood brain barrier are desirable.

"EC50," or "effective concentration 50," is a measurement of the substrate concentration that results in a turnover rate 50% of the maximal turnover rate for the substrate (0.5 $V_{max}$).

A plasma membrane containing a monolayer of cells in physical contact with each other and having different sets of proteins embedded in the plasma membranes facing either side of the monolayer is described as being "polarized". For example, brain microvessel endothelial cells in the blood brain barrier have a luminal side facing capillaries and exposed to blood, and an abluminal side facing cells of the central nervous system and exposed to cerebrospinal fluid. The luminal plasma membrane contains a different set of transmembrane and membrane-associated components than the abluminal plasma membrane of the same cell. Brain microvessel endothelial cells in culture can also be polarized, where the cells form a monolayer in culture that has a luminal and abluminal side. MDCK cells, when grown on filter membranes in transwell dishes, form a polarized monolayer in which one side of the monolayer is the apical side and the other is the basolateral side.

"Sustained release" refers to release of a therapeutic or prophylactic amount of a drug or an active metabolite thereof over a period of time that is longer than a conventional formulation of the drug. For oral formulations, the term "sustained release" typically means release of the drug within the gastrointestinal tract lumen over a period of from about 2 to about 30 hours, more typically over a period of about 4 to about 24 hours. Sustained release formulations achieve therapeutically effective concentrations of the drug in the systemic blood circulation over a prolonged period of time relative to that achieved by oral administration of a conventional formulation of the drug. "Delayed release" refers to release of the drug or an active metabolite thereof into the gastrointestinal lumen after a delay time period, typically a delay of about 1 to about 12 hours, relative to that achieved by oral administration of a conventional formulation of the drug.

The phrase "specifically binds" when referring to a substrate or ligand of the CAT1 transporter refers to a specific interaction between a substrate or ligand and the CAT1 transporter in which the substrate or ligand binds preferentially with the CAT1 transporter and does not bind in a significant amount to most or any other proteins present in a biological sample. A substrate or ligand that specifically binds to the CAT1 transporter often has an association constant of 10-$10^3$ $M^{-1}$, $10^5 M^{-1}$, $10^6 M^{-1}$, or $10^7 M^{-1}$, preferably $10^8 M^{-1}$ to $10^9$ $M^{-1}$ or higher. However, some substrates or ligands of CAT1 transporters have much lower affinities and yet the binding can still be shown to be specific. Substrates of CAT1 can specifically bind to CAT1 and other proteins such as efflux transporters without specifically binding to other proteins.

"$P_{app}$," or "apparent permeability," is a value that reflects the permeability of a test compound through a cell layer such as a polarized monolayer. The equation for determining $P_{app}$ is as follows:

$$P_{app} = \frac{V \cdot dC}{A \cdot C_0 dt} (cm/sec)$$

where,
V=volume of receiving chamber (in $cm^3$, i.e., ml);
dC/dt=steady state rate of appearance of applied compound in receiving chamber after primary lag time (in μM/sec);
$C_0$=concentration of compound in the donor chamber (in μM); and
A=area of the cell layer (in $cm^2$).

"Allelic variants" at the DNA level are the result of genetic variation between individuals of the same species. Some allelic variants at the DNA level that cause substitution, deletion or insertion of amino acids in proteins encoded by the DNA result in corresponding allelic variation at the protein level.

"Cognate forms" of a gene refers to variation between structurally and functionally related genes between species. For example, the human gene showing the greatest sequence identity and closest functional relationship to a mouse gene is the human cognate form of the mouse gene.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

Another example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information web site. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra.). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. For identifying whether a nucleic acid or polypeptide is within the scope hereof, the default parameters of the BLAST programs are suitable. The BLASTN program (for nucleotide sequences) uses as defaults a word length (W) of 11, an expectation (E) of 10, M=5, N=−4, and a comparison of both strands. For amino acid sequences, the BLASTP program uses as defaults a word length (W) of 3, an expectation (E) of 10, and the BLOSUM62 scoring matrix. The TBLASTN program (using protein sequence for nucleotide sequence) uses as defaults a word length (W) of 3, an expectation (E) of 10, and a BLOSUM 62 scoring matrix (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

DETAILED DESCRIPTION

I. General

CAT1 is shown herein to be expressed at high levels in brain microvessel endothelial cells. This finding can be used to generate or isolate conjugates and agents having neuropharmacological or imaging activity useful for treatment, prophylaxis or diagnosis of neurological diseases. The invention provides methods of identifying agents, conjugates or conjugate moieties that are substrates for CAT1. For therapeutic purposes, agents or conjugates having inherent neuropharmacologic activity can be screened to determine whether they are substrates for CAT1. Alternatively, a conjugate moiety lacking such activity can be screened, and linked to a neuropharmacologic agent after screening. Agents or conjugates that have both neuropharmacologic activity and are substrates for CAT1 are preferentially transported into the CNS via CAT1 transporters after administration to a patient. Such an agent or conjugate by itself or in combination with another agent is effective in treatment or prophylaxis of a neurological disease. An analogous approach is used for imaging features of the brain. Agents and conjugates that have an imaging component and are substrates for CAT1 are preferentially transported into the CNS via CAT1 transporters. The imaging component is then detected by various methods such as detecting radioactive decay of the imaging component. The agents and conjugates can be used to image brain tumors overexpressing the CAT1 transporter. Optionally, the agents or conjugates have inherent affinity for, or are provided with a conjugate moiety that confers affinity for, a particular antigen or cell type within the brain. For example, the agents or conjugates can be provided with a targeting moiety to Aβ to allow imaging of plaques in Alzheimer's patients.

II. CAT1 Transporter

The family of amino acid permease transporters contains at least 13 members in humans (SLC7A1-13). Amino acid permease transporters have 12 putative transmembrane domains, with both the amino and carboxy termini located on the cytoplasmic side. One member of this family is CAT1 (SLC7A1), which mediates the cellular uptake of cationic amino acids such as lysine, arginine, and ornithine. CAT1 transport is dependent on the plasma transmembrane potential.

It is now shown that CAT1 is highly expressed in brain microvessel endothelial cells. It is desirable to generate agents, conjugates, and conjugate moieties for transport into the CNS that have activity for CAT1 due to this high expression level. The GenBank accession number for human CAT1 is NM_003045 (SEQ ID NO: 1). Unless otherwise apparent from the context, reference to a transporter includes the amino acid sequence described in or encoded by the GenBank reference number NM_003045, and, allelic, cognate and induced variants and fragments thereof retaining essentially the same transporter activity. Usually such variants show at least 90% sequence identity to the exemplary Genbank nucleic acid or amino acid sequence.

III. Methods of Screening to Identify CAT1 Substrates

Agents known or suspected to have a neuropharmaceutical activity or to comprise an imaging component can be screened directly for their capacity to act as substrates of CAT1. Alternatively, conjugate moieties can be screened as substrates, and the conjugate moieties are then linked to a neuropharmaceutical agent or imaging component. In such methods, the conjugate moieties can optionally be linked to a neuropharmaceutical agent or imaging component, or other molecule during the screening process. If another molecule is used in place of a neuropharmaceutical agent or imaging component, the molecule can be chosen to resemble the structure of a neuropharmaceutical agent or imaging component ultimately intended to be linked to the conjugate moiety for neuropharmaceutical use. Alternatively, a conjugate moiety can be screened for a substrate activity alone and linked to a neuropharmaceutical agent or imaging component after screening.

Preferred substrates for CAT1 are amino acids such as arginine, lysine, ornithine, N-Me-arginine, and di-Me-arginine (see, e.g., Deves and Boyd, 1998, Transporters for Cationic Amino Acids in Animal Cells: Discovery, Structure, and Function, Physiological Reviews, 78:2, 847-545). The structure of each compound is depicted in FIG. 1.

Arginine, lysine, ornithine, N-Me-arginine, and di-Me-arginine are examples of CAT1 substrates that are candidates for conjugation to therapeutic neuropharmaceutical agents, cytotoxic neuropharmaceutical agents and imaging components.

In some screening methods, the cells are transfected with DNA encoding the CAT1 transporter. LLCPK (porcine kidney epithelial), HEK (human embryonic kidney), and CHO (Chinese hamster ovary) cells, for example, are suitable for transfection. Oocytes can be injected with CAT1 cRNA to express the CAT1 transporter. In some methods, the only transporter expressed by the cells is the CAT1 transporter. In other methods, cells express CAT1 in combination with other transporters. In still other methods, agents, conjugate moieties, or conjugates are screened on different cells expressing different transporters. Agents, conjugate moieties, or conjugates can be screened either for specificity for the CAT1 transporter or for transport into cells endogenously expressing a plurality of transporters. In some methods, the results of a screening method (e.g., a competition uptake, exchange or direct uptake assay) using a cell expressing the CAT1 transporter can be compared with the results of a control cell(s) lacking the CAT1 transporter or in the presence of a specific inhibitor of the CAT1 transporter.

In some methods, cells endogenously expressing the CAT1 transporter are used. Brain microvessel endothelial cells, for example, endogenously express the CAT1 transporter, as demonstrated in Example 1. Agents, conjugate moieties, or conjugates can be screened for transport into cultured brain microvessel endothelial cells. Passaging cultures of brain microvessel endothelial cells typically causes the cells to lose differentiation characteristics such as the ability to form tight junctions. The propensity of passaged cells to lose differentiation characteristics can be avoided through the use of brain microvessel endothelial cells that are transformed with an SV40 large T antigen (see Terasaki et al., Drug Discovery Today 8:944-954 (2003)). Inducible expression of the SV40 large T antigen allows cells to divide when the antigen is expressed and differentiate when the antigen is not expressed. Brain microvessel endothelial cells can be isolated from animals transgenic for the SV40 large T antigen, which can be expressed in a temperature-sensitive fashion. The cells are stimulated to divide by being cultured at the temperature at which the antigen is expressed. Once the cells have formed a monolayer, they are placed at a temperature at which the antigen is not expressed, causing the cells to stop dividing and differentiate. Differentiation results in the formation of tight junctions and the polarization of the plasma membranes. Monolayers of polarized cells are tested for the ability to transport agents, conjugates or conjugate moieties.

In some methods, the ability of an agent, conjugate, or conjugate moiety to specifically bind to the CAT1 transporter is tested. A known substrate of the CAT1 transporter and the agent, conjugate, or conjugate moiety are added to cells expressing the CAT1 transporter. The amount or rate of transport of the substrate in the presence of the agent, conjugate, or conjugate moiety is compared to the amount or rate of transport of the agent, conjugate, or conjugate moiety in the absence of the test compound. If the amount or rate of transport of the substrate is decreased by the presence of the agent, conjugate, or conjugate moiety, the agent, conjugate, or conjugate moiety binds the CAT1 transporter. Agents, conjugates or conjugate moieties that bind the CAT1 transporter can be further analyzed to determine if they are transported by the CAT1 transporter or only adhere to the exterior of the transporter. Agents, conjugates or conjugate moieties that are transported by the CAT1 transporter can be further tested to determine if they are transported from one side of a monolayer of polarized cells to the other side, such as a monolayer of brain microvessel endothelial cells. Agents and conjugates having neuropharmaceutical activity and that are transported by the CAT1 transporter can be used to form pharmaceutical compositions. Conjugate moieties that are transported by the CAT1 transporter can be linked to a therapeutic or cytotoxic neuropharmaceutical agent or an imaging component.

Transport of a compound into a cell can be detected by detecting a signal from within a cell from any of a variety of reporters. The reporter can be as simple as a label such as a fluorophore, a chromophore, or a radioisotope. Confocal imaging can also be used to detect internalization of a label as it provides sufficient spatial resolution to distinguish between fluorescence on a cell surface and fluorescence within a cell; alternatively, confocal imaging can be used to track the movement of compounds over time. In another approach, transport of a compound is detected using a reporter that is a substrate for an enzyme expressed within a cell. Once the compound is transported into the cell, the substrate is metabolized by the enzyme and generates an optical signal that can be detected. Light emission can be monitored by commercial PMT-based instruments or by CCD-based imaging systems. In addition, assay methods utilizing liquid chromatography-mass spectroscopy (LC-MS-MS) detection of the transported compounds or electrophysiological signals indicative of transport activity are also employed. Mass spectroscopy is a powerful tool because it allows detection of very low concentrations of almost any compound, especially molecules for which a radiolabeled version is not available. It can also be used to distinguish substrates from non-transported ligands. These same detection methods can be used to determine if a compound is transported from one side of a monolayer of polarized cells to the other side by administering the compound to one side of the monolayer and sampling the media on the other side of the monolayer after a predetermined period of time.

In some methods, multiple agents, conjugates or conjugate moieties are screened simultaneously and the identity of each agent, conjugate, or conjugate moiety is tracked using tags linked to the agents, conjugates or conjugate moieties. In some methods, a preliminary step is performed to determine binding of an agent, conjugate, or conjugate moiety to a transporter. Although not all agents, conjugates or conjugate moieties that bind to a transporter are substrates of the transporter, observation of binding is an indication that allows one to reduce the number of candidates from an initial repertoire. In some methods, the transport rate of an agent, conjugate, or conjugate moiety is tested in comparison with the transport rate of a reference substrate for that transporter. For example, arginine, a natural substrate of CAT1, can be used as a reference. The comparison can be performed in separate parallel assays in which an agent, conjugate, or conjugate moiety under test and the reference substrate are compared for uptake on separate samples of the same cells. Alternatively, the comparison can be performed in a competition format in which an agent, conjugate, or conjugate moiety under test and the reference substrate are applied to the same cells. Typically, the agent, conjugate, or conjugate moiety and the reference substrate are differentially labeled in such assays.

In comparative assays, the $V_{max}$ of an agent, conjugate, or conjugate moiety tested can be compared with that of a reference substrate. If an agent, conjugate moiety, or conjugate has a $V_{max}$ of at least 1%, 5%, 10%, 20%, and most preferably at least 50% of the reference substrate for the CAT1 transporter, then the agent, conjugate moiety, or conjugate is also a substrate for the CAT1 transporter. If transport of the agent, conjugate moiety, or conjugate into the CNS is desired, a higher $V_{max}$ of the agent, conjugate moiety, or conjugate relative to that of the reference substrate is preferred. Therefore, agents, conjugate moieties, or conjugates having $V_{max}$'s of at least 1%, 5%, 10%, 20%, 50%, 100%, 150%, or 200% (i.e., two-fold) of the $V_{max}$ of a reference substrate (e.g., arginine) for the transporter are screened in some methods. The components to which conjugate moieties are linked can by themselves show little or no detectable substrate activity for the transporter (e.g., $V_{max}$ relative to that of a reference substrate of less than 0.1% or 1%). Preferred agents, conjugates, or conjugate moieties have a $V_{max}$ for CAT1 that is at least 5% of the $V_{max}$ for CAT1 of arginine. Preferred conjugates comprising a neuropharmaceutical agent or imaging component linked to a conjugate moiety preferably have a greater $V_{max}$ for CAT1 than the neuropharmaceutical agent or imaging component alone.

Having determined that an agent, conjugate, or conjugate moiety is a substrate for CAT1, a further screen can be performed to determine its therapeutic activity in treatment or prophylaxis of a disease, or its cytotoxic activity against brain tumor cells. Usually the disease is neurological (i.e., the pathology occurs in the CNS). Alternatively, the diseased tissue is non-CNS tissue but is responsive to treatment by an agent that exerts a pharmacological effect on the CNS that in turn causes an effect on the diseased non-CNS tissue, such as an effect caused by the release of hormones from the CNS. Diseases of this type are also considered to be diseases of the CNS unless otherwise apparent from context. If the agent, conjugate, or conjugate moiety does not have inherent therapeutic or cytotoxic activity, it is first linked to another chemical component having such therapeutic or cytotoxic properties. The agent, conjugate, or conjugate moiety is then contacted with cells expressing CAT1. The contacting can be performed either on a population of cells in vitro, or the brain microvessel endothelial cells of a test animal via administration of the agent, conjugate, or conjugate moiety to a test animal. The therapeutic or cytotoxic activity of the agent, conjugate, or conjugate moiety is then determined from established protocols for that particular disease. Optionally, the effect of the agent, conjugate, or conjugate moiety can be compared with a placebo.

A further screen can be performed to determine toxicity of the agent, conjugate, or conjugate moiety to normal cells. The agent, conjugate, or conjugate moiety is administered to a laboratory animal that is preferably in an un-diseased state. Various tissues of the animal, such as liver, kidney, heart and brain are then examined for signs of pathology. Cells in the animal can also be analyzed for uptake of the agent, conjugate, or conjugate moiety.

IV. Iterative Modification and Testing of CAT1 Substrates

Having determined that an agent, conjugate, or conjugate moiety is a substrate for CAT1, the agent, conjugate, or conjugate moiety can be modified to improve its properties as a substrate. The modified agent, conjugate, or conjugate moiety is then tested for transport by CAT1. Modified agents, conjugates, or conjugate moieties that are transported by CAT1 at a higher $V_{max}$ compared to the unmodified agents, conjugates, or conjugate moieties are preferred. The process of modifying agents, conjugates or conjugate moieties and testing for transport by CAT1 can be repeated until a desired level of transport is reached.

Agents, conjugates or conjugate moieties that are substrates of CAT1 can also be modified for decreased capacity to be transported out of cells by efflux transporters. An agent, conjugate, or conjugate moiety transported by CAT1 is assayed to determine whether it is also a substrate for one or more efflux transporters. If the agent, conjugate, or conjugate moiety is transported by an efflux transporter, the agent, conjugate, or conjugate moiety is modified and tested for both reduced transport by an efflux transporter and retention of CAT1 substrate activity.

In some instances, the specific efflux transporter responsible for transporting an agent, conjugate, or conjugate moiety is known. The agent, conjugate, or conjugate moiety is modified, preferably by addition of a chemical group that differs in chemical characteristics from other known substrates of the efflux transporter. The modified agent, conjugate, or conjugate moiety is then tested for retained capacity to be transported by CAT1 and a diminished capacity to be transported by an efflux transporter. It is not necessary that the modified agent, conjugate, or conjugate moiety retain the same kinetic properties of CAT1 transporter substrate as the unmodified agent, conjugate, or conjugate moiety as long as some CAT1 substrate activity is retained. Examples of efflux transporters are the P-glycoprotein (PgP), multidrug resistance protein (MRP1), and breast cancer resistance protein (BCRP). Preferred agents, conjugates, or conjugate moieties have a CAT1 transport:efflux transport ratio of at least 1.1:1.0, more preferably, 2.0:1.0, and more preferably 5.0:1.0 and more preferably 10.0:1.0 or higher at a given concentration of agent, conjugate, or conjugate moiety.

Efflux transporter activity can be measured in several ways. First, functional assays can be performed in which interaction of compounds with efflux transporters is measured by stimulation of efflux transporter ATPase activity in cellular membrane fragments or vesicles. Second, competition assays can be performed in which test compounds compete with known efflux substrates in whole cells. Third, direct transport assays can be performed in which the transport of compounds is measured across a polarized monolayer of cells. Other assays besides these three can also be used to directly or indirectly measure the efflux substrate characteristics of a test compound.

The efflux transporter ATPase assay is based on the fact that most efflux substrates increase the ATPase activity of efflux transporters upon binding. In one type of assay, Baculovirus membrane fragments or vesicles containing an efflux transporter such as PgP, as well as control membrane fragments or vesicles not containing the efflux transporter, are either prepared or obtained from commercial suppliers. The ATPase activity of the membrane fragments or vesicles is measured in the presence of various concentrations of the test compound. An agent, conjugate, or conjugate moiety that is transported by CAT1 is added to the ATPase assay reaction and the amount of ATPase activity is measured at various concentrations of agent, conjugate, or conjugate moiety. Parallel experiments are performed in which ATPase activity is measured under addition of the same concentrations of modified agent, conjugate, or conjugate moiety that retain CAT1 substrate activity. Reduced ATPase activity caused by the modified agent, conjugate, or conjugate moiety compared to the unmodified agent, conjugate, or conjugate moiety indicates that the modified agent, conjugate, or conjugate moiety is a better candidate for retention in the CNS.

In the competition assay, the test compound is assayed for competition with a known efflux substrate. For example, calcein-AM is a non-fluorescent compound that is a substrate of PgP and MRP1. Calcein-AM is initially loaded into the cells, for example, by transport by passive diffusion. Cells expressing these efflux transporters actively efflux nearly all of the calcein-AM that is present in the cells. However, when other efflux transporter substrates are present, these other substrates compete with calcein-AM for efflux, resulting in more calcein-AM accumulating inside the cells. Intracellular esterases convert the non-fluorescent calcein-AM to fluorescent calcein, which can be measured spectrophotometrically. An agent, conjugate, or conjugate moiety that is transported by CAT1 is loaded into efflux transporter-containing cells by either CAT1 transport or passive diffusion. Calcein-AM is also loaded into the cells by active transport or transport by passive diffusion. Accumulation of calcein-AM is measured and compared to the amount of accumulation in the absence of the agent, conjugate, or conjugate moiety. Parallel experiments are performed in which a modified agent, conjugate, or conjugate moiety that is transported by CAT1 is loaded into the cells. Accumulation of calcein-AM is measured and compared to the amount of accumulation in the absence of the modified agent, conjugate, or conjugate moiety. Decreased calcein-AM accumulation inside the cells caused by the presence of a modified agent, conjugate, or conjugate moiety compared to calcein-AM accumulation in the presence of unmodified agent, conjugate, or conjugate moiety indicates that the modified agent, conjugate, or conjugate moiety is a better candidate for retention inside the CNS.

The cells used for competition assays can be cells that either express a high endogenous level of the efflux transporter of interest or are transformed with an expression vector containing the efflux transporter gene. Suitable cell lines for efflux assays are, for example, HEK and MDCK cell lines into which the PgP gene has been transfected, or MES-SA/Dx5 uterine sarcoma cells grown in the presence of 500 nM doxorubicin, which express a high endogenous level of PgP. These cells can optionally be transfected with the CAT1 transporter gene. Preferred cells express one or more efflux transporter genes such as PgP and the CAT1 gene, either endogenously or through transfection of expression vectors.

A third type of efflux transporter assay is the cellular transwell monolayer efflux assay. In this assay, cells expressing efflux transporters, such as MDCK, CHO, HEK, and LLCPK cells containing the TREx-PgP expression vector (Invitrogen Inc., Carlsbad, Calif.), are seeded and grown in transwell dishes on filter membranes made of substances such as polycarbonate. The cells form a polarized monolayer. The transwell dishes have apical and basolateral chambers that are separated by the filter membrane on which the polarized monolayer is situated. Assays are performed by placing a test compound in either the apical or basolateral chamber, followed by sampling the opposite chamber after a predetermined period of time such as 60-120 minutes and measuring the amount of the test compound. The test compound can be measured by methods such as radiolabel detection or LC-MS-MS analysis. Assays are performed in the presence and absence of an efflux transporter inhibitor or competitor. Efflux transporter inhibitors or competitors increase apical to basolateral transport and decrease basolateral to apical transport of compounds that are efflux transporter substrates. Apparent permeability ($P_{app}$) of test compounds is measured. Test compounds that are substrates of efflux transporters generate a $P_{app}$ (basolateral to apical)/$P_{app}$ (apical to basolateral) ratio of greater than 2.0, while test compounds that are not substrates generate a ratio of 1.5 or less. Test compounds that generate ratios between 1.5 and 2.0 require additional testing to determine if they are efflux transporter substrates. An agent, conjugate, or conjugate moiety that is a CAT1 substrate and also generates a ratio of greater than 2.0 can be modified. A modified agent, conjugate, or conjugate moiety that retains CAT1 substrate activity and generates a lower ratio compared to the unmodified agent, conjugate, or conjugate moiety indicates that the modified agent, conjugate, or conjugate moiety is a better candidate for retention inside the CNS.

An additional screen can be performed to determine whether agents, conjugates or conjugate moieties have substantial capacity for passive diffusion across the brain microvessel endothelial cells making up the blood brain barrier. Such an assay can be performed using cells lacking CAT1 transporters. That is, the agents, conjugates or conjugate moieties are exposed to cells that lack CAT1 transporters, and the amount of agents, conjugates, or conjugate moieties that are present inside the cell is measured.

V. Modification of Compounds having Non-Neuropharmacologic Activity

In some instances it is desirable to modify an agent to reduce its capacity to be transported from the blood into the brain. Reduced capacity to enter the brain is desirable for agents having a pharmacological activity that is useful in a tissue outside the CNS, but which causes undesired side effects when the agent enters the CNS. Most typically, such agents are drugs administered to treat a non-neurological disease, and which exert a useful therapeutic pharmacological effect on cells, tissues, or molecules located outside of the CNS. When such drugs are transported from the blood into the brain, serious side effects can occur. Many known drugs exhibit undesirable side effects from penetrating the CNS. Examples include drowsiness experienced by patients taking antihistamines, nonsteroidal anti-inflammatory drugs (NSAIDS), anti-asthmatics, and antihypertensives.

Some methods are performed on an agent having an intended site of pharmacological activity that is located outside of the CNS. The agent can be known or suspected to enter the CNS. In some instances, the agent is known to be transported by CAT1. The agent is covalently attached to a conjugate moiety and the resulting conjugate is tested for transport into the brain. The assay can be performed on brain microvessel endothelial cells, cells transformed with a CAT1 expression vector, a polarized monolayer of cells, or an actual blood brain barrier via administration to a test animal. Transport of the conjugate is then compared with transport of the agent alone (i.e., without the conjugate moiety). Conjugates having a lower $V_{max}$ for transport than the agent alone are less likely to exhibit undesirable CNS side effects caused by unwanted transport from the blood into the brain. For example, preferred conjugates include those having a lower $V_{max}$ for transport by CAT1 than the agent alone.

Some methods comprise providing an agent having a pharmacological activity, wherein the pharmacological activity is useful for treating a disease present in a tissue other than the CNS, and the pharmacological activity results in undesired side effects in the CNS if the agent enters the CNS, modifying the agent, providing a cell expressing at least one transporter protein that transports substrates across the blood brain barrier, contacting the cell with the modified agent, and determining whether the modified agent passes through the plasma membrane via the transporter protein with a lower $V_{max}$ than the agent, a lower $V_{max}$ indicating that the modification decreases the capacity of the modified agent relative to the agent to cross the blood brain barrier, thereby decreasing undesired side effects in the CNS. In some methods the at least one transporter protein is CAT1. In some methods the cell is transformed or injected with a nucleic acid encoding a transporter or the cell is a brain microvessel endothelial cell. In some methods the modifying step comprises linking the agent to a conjugate moiety to form a conjugate, preferably wherein the conjugate moiety is an inhibitor of the CAT1 transporter.

Other methods comprise providing an agent having a pharmacological activity, wherein the pharmacological activity is useful for treating a disease present in a tissue other than the CNS, and the pharmacological activity results in undesired side effects in the CNS if the agent enters the CNS, modifying the agent, providing a cell expressing at least one efflux transporter protein that transports substrates out of the CNS, contacting the cell with the modified agent, and determining whether the modified agent is transported by the at least one efflux transporter protein with a higher $V_{max}$ than the agent, a higher $V_{max}$ indicating that the modification increases the capacity of the modified agent relative to the agent to be transported out of the CNS, thereby decreasing undesired side effects in the CNS. In some methods the at least one efflux transporter protein is P-glycoprotein (PgP), multidrug resistance protein (MRP1), or breast cancer resistance protein (BCRP). In some methods the cell is transformed or injected with a nucleic acid encoding an efflux transporter or the cell is a brain microvessel endothelial cell, a kidney-derived cell, or a uterine sarcoma cell. In some methods the modifying step comprises linking the agent to a conjugate moiety to form a conjugate, preferably wherein the conjugate moiety is a substrate of the efflux transporter.

VI. Sources of Neuropharmaceutical Agents, Imaging Components, and Conjugate Moieties Therapeutic neuropharmaceutical agents, cytotoxic neuropharmaceutical agents, imaging components and conjugate moieties can be obtained from natural sources such as, e.g., marine microorganisms, algae, plants, and fungi. Alternatively, these compounds can be from combinatorial libraries, including peptides or small molecules, or from existing repertories of chemical compounds synthesized in industry, e.g., by the chemical, pharmaceutical, environmental, agricultural, marine, cosmeceutical, drug, and biotechnological industries. Neuropharmaceutical compounds can include proteins, antibiotics, adrenergic agents, anticonvulsants, small molecules, nucleotide analogs, chemotherapeutic agents, anti-trauma agents, peptides and other classes of agents used in treatment or prophylaxis of a neurological disease. Examples of such proteins include CD4 (including soluble portions thereof), growth factors (e.g., nerve growth factor and interferon), dopamine decarboxylase and tricosanthin. Examples of such antibiotics include amphotericin B, gentamycin sulfate, and pyrimethamine. Examples of such adrenergic agents (including blockers) include dopamine and atenolol. Examples of such chemotherapeutic agents include adriamycin, methotrexate, cyclophosphamide, etoposide, and carboplatin. An example of an anticonvulsant that can be used is valproate and an anti-trauma agent that can be used is superoxide dismutase. Examples of such peptides are somatostatin analogues and enkephalinase inhibitors. Nucleotide analogs that can be used include azido thymidine (hereinafter AZT), dideoxy Inosine (ddI), and dideoxy cytodine (ddc).

Typically if an agent is being screened as a substrate, the agent is known or suspected to have an inherent therapeutic neuropharmaceutical, cytotoxic neuropharmaceutical or imaging activity. If a conjugate is being screened, the conjugate usually comprises such an agent or component. If a conjugate moiety is being screened, the conjugate moiety typically lacks a therapeutic, cytotoxic or imaging activity and an agent or component that has this activity is added after screening.

Suitable cytotoxic agents for incorporation into conjugates or linkage to conjugate moieties after screening include platinum, nitrosourea, nitrogen mustard, nitroimidazole, and a phosphoramide group that is only cytotoxic to brain tumor cells. The choice of imaging component depends on the means of detection. For example, a fluorescent imaging component is suitable for optical detection. A paramagnetic imaging component is suitable for topographic detection without surgical intervention. Radioactive labels can also be detected using positron emission tomography or single photon emission computed tomography.

The agents, conjugates or conjugate moieties to be screened, optionally linked to a neuropharmaceutical agent or an imaging component if not inherently present, are preferably small molecules having molecular weights of less than about 2500 Da, preferably less than about 2000 Da, preferably less than about 1500 Da, preferably less than about 1000 Da and preferably less than about 500 Da.

VII. Linkage of Neuropharmaceutical Agents or Imaging Components to Substrates

Conjugates can be prepared either by direct conjugation of a neuropharmaceutical agent or an imaging component to a substrate of CAT1 with a covalent bond (optionally cleavable in vivo), or by covalently coupling a difunctionalized linker precursor with the neuropharmaceutical agent or imaging component and substrate. The linker precursor is selected to contain at least one reactive functionality that is complementary to at least one reactive functionality on the neuropharmaceutical agent or imaging component and at least one reactive functionality on the substrate. Optionally, the linker is cleavable. Suitable complementary reactive groups are well known in the art as illustrated below:

COMPLEMENTARY BINDING CHEMISTRIES

| First Reactive Group | Second Reactive Group | Linkage |
|---|---|---|
| hydroxyl | carboxylic acid | ester |
| hydroxyl | haloformate | carbonate |
| thiol | carboxylic acid | thioester |
| thiol | haloformate | thiocarbonate |
| amine | carboxylic acid | amide |
| hydroxyl | isocyanate | carbamate |
| amine | haloformate | carbamate |
| amine | isocyanate | urea |
| carboxylic acid | carboxylic acid | anhydride |
| hydroxyl | phosphorus acid | phosphonate or phosphate ester |

The same methods of chemical modification can be used to form conjugates for the purpose of inhibiting transport into the CNS, for inhibiting efflux from the CNS, or for enhancing efflux from the CNS.

VIII. Pharmaceutical Compositions

The above screening processes can identify one or more types of compounds that can be incorporated into pharmaceutical compositions. These compounds include agents that are both substrates for CAT1 and have an inherent neuropharmaceutical activity or imaging activity. The compounds also include conjugates in which a neuropharmaceutical agent or imaging component is linked to a substrate for CAT1. Conjugates comprising an agent with a pharmacological activity and a conjugate moiety having decreased substrate capacity for CAT1 relative to the agent alone are also provided for the purpose of reducing transport of the agent into the CNS, where the agent would confer undesired side effects.

One or more of the above entities can be combined with pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, buffered water, physiological saline, phosphate buffered saline (PBS), Ringer's solution, dextrose solution, and Hank's solution. In addition, the pharmaceutical composition or formulation can also include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents, detergents and the like (see, e.g., Remington's Pharmaceutical Sciences, Mace Publishing Company, Philadelphia, Pa., 17th ed. (1985); for a brief review of methods for drug delivery, see, Langer, Science 249:1527-1533 (1990); each of these references is incorporated by reference in its entirety).

Pharmaceutical compositions can be administered orally, intranasally, intradermally, subcutaneously, intrathecally, intramuscularly, topically, intravenously, or injected directly to a site of cancerous tissue. For parenteral administration, the compounds disclosed herein can be administered as injectable dosages of a solution or suspension of the compound in a physiologically acceptable diluent with a pharmaceutical carrier which can be a sterile liquid such as water, oils, saline, glycerol, or ethanol. Additionally, auxiliary substances, such as wetting or emulsifying agents, surfactants, pH buffering substances and the like can be present in the pharmaceutical compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or a copolymer thereof for enhanced adjuvant effect, as discussed above (see Langer, Science 249, 1527 (1990) and Hanes, Advanced Drug Delivery Reviews 28, 97-119 (1997)). The pharmaceutical compositions disclosed herein can be administered in the form of a depot injection or implant preparation that can be formulated in such a manner as to permit a sustained or pulsatile release of the active ingredient.

Pharmaceutical compositions for oral administration can be in the form of e.g., tablets, pills, powders, lozenges, sachets, cachets, elixirs, suspensions, emulsions, solutions, or syrups. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methylcellulose. Preserving agents such as methyl- and propylhydroxy-benzoates; sweetening agents; and flavoring agents can also be included. Depending on the formulation, compositions can provide quick, sustained, or delayed release of the active ingredient after administration to the patient. Polymeric materials can be used for oral sustained release delivery (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, J Macromol. Sci. Rev. Macromol Chem. 23:61; see also Levy et al., 1985, Science 228: 190; During et al., 1989, Ann. Neurol. 25:351; Howard et al., 1989, J. Neurosurg. 71:105). Sustained release can be achieved by encapsulating conjugates within a capsule, or within slow-dissolving polymers. Preferred polymers include sodium carboxymethylcellulose, hydroxypropylcellulose, hydroxypropylmethylcellulose, and hydroxyethylcellulose (most preferred, hydroxypropyl methylcellulose). Other preferred cellulose ethers have been described (Alderman, Int. J. Pharm. Tech. & Prod. Mfr., 1984, 5(3), 1-9). Factors affecting drug release have been described in the art (Bamba et al., Int. J. Pharm., 1979, 2, 307). For administration by inhalation, the compounds for use according to the disclosures herein are conveniently delivered in the form of an aerosol spray preparation from pressurized packs or a nebulizer, with the use of a suitable propellant, e.g., dichlorodifluoromethane, trichlorofluoromethane, dichlorotetrafluoroethane, carbon dioxide or other suitable gas, or from propellant-free, dry-powder inhalers. In the case of a pressurized aerosol the dosage unit can be determined by providing a valve to deliver a metered amount. Capsules and cartridges of, e.g., gelatin for use in an inhaler or insufflator, can be formulated containing a powder mix of the compound and a suitable powder base such as lactose or starch.

Effective dosage amounts and regimes (amount and frequency of administration) of the pharmaceutical compositions are readily determined according to any one of several well-established protocols. For example, animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example.

The components of pharmaceutical compositions are preferably of high purity and are substantially free of potentially harmful contaminants (e.g., at least National Food (NF) grade, generally at least analytical grade, and more typically at least pharmaceutical grade).

To the extent that a given compound must be synthesized prior to use, the resulting product is typically substantially free of any potentially toxic agents, particularly any endotoxins, which may be present during the synthesis or purification process. Compositions are usually made under GMP conditions. Compositions for parenteral administration are usually sterile and substantially isotonic.

IX. Methods of Treatments

Pharmaceutical compositions disclosed herein are used in methods of treatment of prophylaxis of neurological diseases. Examples of such diseases amenable to treatment are cancer (e.g., brain tumors), Acquired Immune Deficiency Syndrome (AIDS), stroke, epilepsy, Parkinson's disease, multiple sclerosis, neurodegenerative disease, trauma, depression, Alzheimer's disease, migraine, pain, seizure disorders, inflammation, and allergic diseases.

Other pharmaceutical compositions disclosed herein are used in methods of treatment and prophylaxis of non-neurological diseases. Examples of such diseases amenable to treatment are cancer (e.g., tumors of non-CNS tissue), inflammation, and allergic diseases.

In prophylactic applications, pharmaceutical compositions are administered to a patient susceptible to, or otherwise at risk of, a disease in an amount and frequency sufficient to eliminate or reduce the risk, lessen the severity, or delay the outset of the disease, including biochemical, histologic, and/or behavioral symptoms of the disease, its complications and intermediate pathological phenotypes presenting during development of the disease. In therapeutic applications, pharmaceutical compositions are administered to a patient suspected of, or already suffering from such a disease in an amount and frequency sufficient to cure, or at least partially arrest, the symptoms of the disease (biochemical, histologic, and/or behavioral), including its complications and intermediate pathological phenotypes in development of the disease. An amount of pharmaceutical composition sufficient to achieve at least one of the above objects is referred to as an effective amount, and a combination of amount and frequency sufficient to achieve at least one of the above objects is referred to as an effective regime.

X. Methods of Imaging

As discussed above, the invention provides conjugates comprising a conjugate moiety, which are substrates of CAT1, linked to an imaging component, as well as agents that are substrates for CAT1 and have an inherent imaging activity. Optionally, the agents also have inherent affinity for a particular antigen or cell type found in the CNS, or the conjugate is provided with an additional conjugate moiety having such affinity. The additional moiety is referred to as a targeting moiety. The targeting moiety can be an antibody or fragment thereof, or any other molecule that specifically binds to a desired antigen or cell type within the brain. The invention further provides pharmaceutical compositions comprising all of these entities. These pharmaceutical compositions can be used for in vivo imaging. The compositions are administered to a patient and preferentially taken up by central nervous system cells after being actively transported from the blood into the brain by brain microvessel endothelial cells expressing CAT1 in the patient. The imaging activity is then detected. In some methods, the imaging component is also a cytotoxic agent. For example many radioisotopes are suitable for both imaging and tumor cytotoxic activity. In such cases, methods of imaging and methods of treatment can be combined. Currently used diagnostic imaging techniques include positron emission tomography (PET), magnetic resonance imaging (MRI), and computed tomography (CT). Actively transported imaging components provide information about, for example, the presence and/or size of a brain tumor. The cell assay methods provided herein can also be used to identify imaging compounds for use outside the CNS, wherein such imaging agents exert undesirable side effect on the CNS.

As can be appreciated from the disclosure above, the present invention has a wide variety of applications. For example, the CAT1 transporter can be used to identify an agent or conjugate that is a substrate for the transporter and that can cross the blood brain barrier and can therefore treat the CNS. The CAT1 transporter also can be used to increase the capacity of an agent to cross the blood brain barrier by identifying a conjugate moiety that is a substrate for the CAT1 transporter and linking the conjugate moiety to the agent. Accordingly, the following examples are offered by way of illustration, not by way of limitation.

EXAMPLES

Example 1

Quantitative PCR Detection of hCAT1 Expression in Brain Endothelial Cells

Quantitative PCR was performed to analyze hCAT1 expression in human brain endothelial cells. Human brain tissue was obtained from epileptic foci surgically removed from human patients. Human brain microvessel endothelial cells were isolated as follows. The brain tissue was washed in 70% ethanol, and placed in sterile phosphate buffered saline. Meninges and surface vessels were removed. Cortical gray matter was minced, placed in preparation medium (1 g/L glucose, 25 mM HEPES, 100 U/ml penicillin, 100 μg/ml streptomycin, 10 μg/ml DNAse I, 1 mg/ml collagenase/dispase, in DMEM, adjusted to a pH of 7.4) and incubated for 1 hour at 37° C. Samples were centrifuged for 10 minutes at 1000× g. Fat, cell debris, and myelin were discarded. The pellet was resuspended in fresh preparation medium and incubated for an additional 3 hours at 37° C. in a shaking bath. Medium was filtered through a 230 μM nylon sieve followed by a 150 μM nylon sieve. Microvessels were collected by retention on a 60 μM nylon sieve. Capillaries were washed with preparation medium, and then pelleted for RNA isolation.

Total RNA was isolated from the brain endothelial cells using the standard protocol for the RNEasy RNA Isolation Kit (Qiagen). Cells were resuspended in RLT lysis buffer at 10 ml per 0.4 grams of cells. Lysates were vortexed and run through a QiaShredder Column (Qiagen) prior to RNA isolation. Once isolated, the RNA was quantified, run on a 1% agarose gel to ensure integrity, and then stored at −80° C.

Prior to cDNA synthesis, total RNA was DNAse I treated to destroy genomic DNA contamination (Invitrogen DNAseI Kit). Twenty microliters of oligo dT primed single-stranded cDNA was then synthesized from 1 μg total RNA (Invitrogen Thermoscript cDNA Synthesis Kit). The cDNA was treated with RNAse H and stored at −20° C.

Quantitative PCR was performed in a 96-well format using the MJ Research DNA Engine Opticon. For each transporter, a pair of 26-base oligonucleotide primers was used to amplify the specific transporter. Primers were designed to recognize the non-conserved 3' ends of hCAT1 transporter mRNA. The single stranded cDNA was used as a template for a PCR reaction containing human, mouse or rat primers and SYBR Green master mix (Applied Biosystems). Fluorescent signal was read and graphed each cycle. A CT value, or cycle threshold value, was determined for each reaction. This value was defined as the point at which the fluorescent signal of the reaction exceeds background fluorescence. Background fluorescence was calculated as 20 standard deviations above the average signal from cycles 3 through 10. Transcript abundance was normalized to GAPDH transcript levels. Averaged results from human hCAT1 amplification experiments are shown below in Table 1. The units of measurement are mRNA transcripts detected per PCR reaction.

TABLE 1

CAT1 mRNA Expression in Human Capillary Endothelial Cells

| | transcripts | forward primer | reverse primer |
|---|---|---|---|
| HUMAN CAT1 | 22,636 | tggcactctcctggcttactcgttgg (SEQ ID NO: 2) | ctcgtcggaagtactggccatctggt (SEQ ID NO: 3) |

The enrichment of hCAT1 transcripts in brain capillary endothelial cells (BMECs) relative to total brain transcripts was also determined by quantitative PCR as described above. Total RNA was isolated from whole brain samples. hCAT1 transcript levels were normalized to GLUT1 transcript levels. GLUT1 transcript levels were determined using the human GLUT1 primers described in Table 3 below. Table 2 below shows the average hCAT1 transcript levels, normalized transcript levels, and ratio of hCAT1 transcripts in BMEC versus human brain cells.

TABLE 2 hCAT1 mRNA Expression in Human Brain Microvessel Endothelial Cells

| | Average BMEC | BMEC % GLUT1 | BMEC:Brain Ratio |
|---|---|---|---|
| CAT1 | 22,718 | 2.8 | 7.1 |
| GLUT1 | 802,859 | 100 | 43.1 |

To confirm the purity of the brain endothelial cell RNA preparations, samples of RNA from each preparation were tested by quantitative PCR for mRNA transcript levels of capillary (GLUT1) and neuronal (BNPI) cell markers. The quantitative PCR analysis was conducted as described above. The primers used are shown in Table 3 below. The results of the control gene transcript quantification are shown in Table 4 below.

TABLE 3

Primers for Quantitative Analysis of Control Genes

| Gene | forward primer | reverse primer |
|---|---|---|
| Human GLUT1 | ggggcatgattggctccttctctgtg (SEQ ID NO: 4) | aggccgcagtacacaccgatgatgaa (SEQ ID NO: 5) |
| Human BNPI | cacccccccgctttcctttatctccag (SEQ ID NO: 6) | ctgctggtaggggagatgtgaagtgg (SEQ ID NO: 7) |

TABLE 4

Control Gene mRNA Transcript Levels

| Control Gene | Human Tissue Source | |
|---|---|---|
| GLUT1 (Capillary marker) | Capillaries | 802859 |
| | Whole Brain | 11120 |
| BNPI (Neuronal marker) | Capillaries | 2614 |
| | Whole Brain | 222285 |

Example 2

Studies of Cloned CAT1 Transporters: Oocyte Expression

To assess transport function of a specific transporter protein, it is preferable to clone the cDNA and express the protein in cells that have low endogenous transport activity. Human CAT1 is cloned by PCR, fully sequenced, and subcloned into plasmids that can be used for expression in mammalian cells or *Xenopus oocytes*. For expression in *Xenopus oocytes*, in vitro CAT1 cRNA is prepared and injected into defoliculated oocytes.

Figure 2:
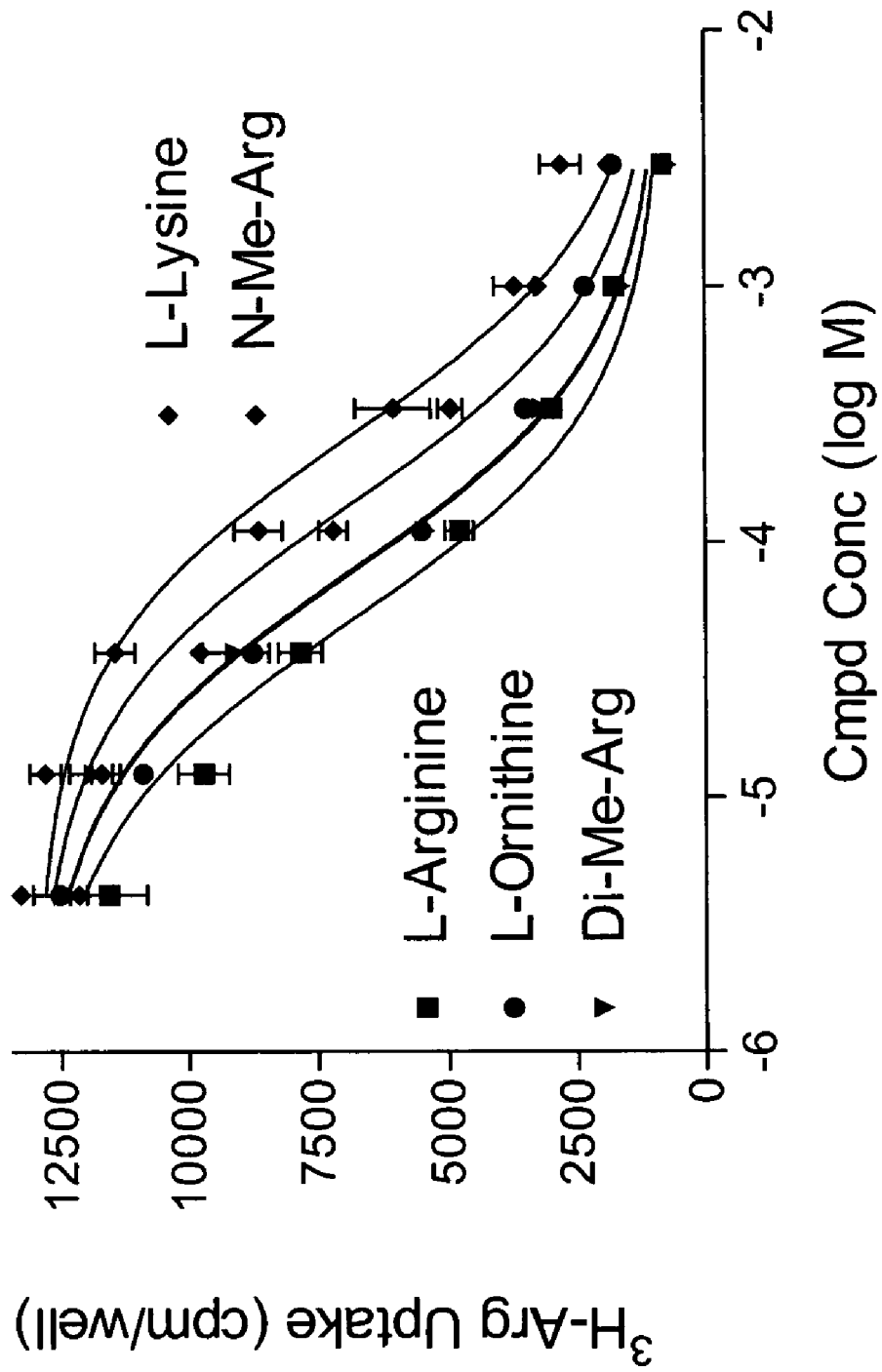
FIG. 2 shows competition assays with LLCPK-TREx-CAT1 cells using $^3$H-arginine as a substrate, and arginine, lysine, ornithine, N-methyl arginine, and dimethyl arginine as competitors.

Oocytes expressing CAT1 protein exhibit higher levels of $^3$H-arginine uptake than noninjected controls, as shown in FIG. 2. To measure directly the uptake of possible substrates, an oocyte uptake assay is performed in which uptake of compounds is measured by mass spectroscopy. For example, uptake of arginine can be measured. Oocytes injected with CAT1 cRNA are incubated at 16-18° C. until maximal transporter expression is reached. Oocytes from the same batch, not injected with cRNA, can be used as a control. A 0.5 mM solution of arginine is prepared in oocyte ringers (ND96) buffer (90 mM NaCl, 10 mM HemiNa HEPES, 2 mM KCl, 1 mM $MgCl_2$, 1.8 mM $CaCl_2$, pH adjusted to 7.4) containing 0.5% bovine serum albumin. The arginine is, for example, administered to pools of 8 oocytes for a 20 minute duration. Following the incubation, the pools of oocytes are washed with 0.5% BSA ND96 buffer and separated into subpools containing, for example, 4 oocytes each. Subpools are homogenized in 150 μl of ice cold 80% MeOH/H$_2$O and lysed manually. Lysates are vortexed before being centrifuged at, for example, 13.2 krpm for 15 minutes. Approximately 110 μl of lysate is removed from the tubes and placed in a 96-well plate and analyzed for arginine concentration by LC-MS-MS.

Samples are analyzed by LC-MS-MS as follows. A specific method can be developed for each test compound, and calibrated against a series of dilutions of known compound concentrations spiked into cellular extract. Measurements are performed using, for example, an API 2000 LC-MS-MS spectrometer equipped with Agilent 1100 binary transporters and a CTC HTS-PAL autosampler. Analyte fragmentation peaks are integrated, for example, using Analyst 1.2 quantitation software, and concentrations are calculated using a calibration curve of signals produced by known concentrations of the compound.

Example 3

Studies of Cloned CAT1 Transporters: CAT1 Transport Currents in Oocytes

The transport of cationic amino acids is driven by the electrochemical gradient and influenced by the transmembrane potential. A negative membrane potential favors the inward movement of cations. This net charge movement can be recorded as current using two-electrode clamping in oocytes expressing CAT 1. The transmembrane potential of oocytes is held between −60 mV and −80 mV and current traces are acquired using PowerLab software (ADInstruments). Full 7-concentration dose-responses are performed for the test compound. Current responses at the highest concentration are normalized to the maximal concentration of the test compound. Half-maximal concentrations are calculated using non-linear regression curve fitting software (Prism) with the Hill co-efficient fixed to 1. To ensure that currents are specific for the over-expressed transporter, all compounds are tested against uninjected oocytes.

Example 4

Competition Assays

To determine whether a compound interacts with the CAT1 transporter, a competition-binding assay is performed. This assay measures how different concentrations of a test compound block the uptake of a radiolabeled substrate such as arginine. The half-maximal inhibitory concentration (IC$_{50}$) for inhibition of transport of a substrate by a test compound is an indication of the affinity of the test compound for the CAT1 transporter. Competition binding studies are performed as follows. Cells endogenously expressing the CAT1 transporter or transfected with a CAT1 expression vector are plated in 96-well plates at 100,000 cells/well and incubated at 37° C. for 24 hours. Radiolabeled arginine (~50,000 cpm/well) is added to each well in the presence and absence of various concentrations of unlabeled arginine in duplicate or triplicate. Plates are incubated at room temperature for 2 minutes. Excess radiolabeled arginine is removed and cells are washed with cold assay buffer. Scintillation fluid is added to each well, and the plates are sealed and counted in a 96-well plate-based scintillation counter. Data can be graphed and analyzed using non-linear regression analysis with Prism Software (GraphPad, Inc., San Diego, Calif.).

Competition binding studies only demonstrate that a molecule interacts with the CAT1 protein, but do not demonstrate whether the molecule is a substrate and is translocated across the plasma membrane, or is a non-transported inhibitor or a non-transported ligand. In order to measure whether test compounds are actively translocated across the membrane, and to determine the maximal transport rate, a direct uptake method is used in which transport of a test compound is measured by mass spectroscopy. For direct uptake measurements using mass spectroscopy, cells are prepared similarly to those used for competition studies (described above). CAT1-expressing cells are washed and incubated with test compounds such as arginine. Excess substrate is removed by washing with cold assay buffer. Cells are lysed with 50% ethanol/water and the cell debris is pelleted by centrifugation. The supernatant is analyzed by LC-MS-MS. As a negative control, uptake is measured in cells not expressing CAT1 or by competition with another compound such as ornithine.

Example 5

Efflux Assays

To determine whether a compound is a substrate for an efflux transporter, an efflux assay is performed. The assay measures whether a test compound interacts with, or is a substrate for, the efflux transporter.

Efflux assays can be performed by adding a test compound to commercial Baculovirus membranes (purchased from BD Biosciences) at various concentrations followed by ATPase activity measurement. A test compound (e.g., agent, conjugate, or conjugate moiety) that is a substrate of the transporter of interest is added to the ATPase assay reaction and the amount of ATPase activity is measured at various concentrations of the test compound. An efflux transporter substrate optionally is used as a control. Parallel experiments optionally can be performed in which ATPase activity is measured under the same conditions by addition of the same concentrations of a modified test compound that retains transporter substrate activity. Reduced ATPase activity caused by the modified test compound compared to the unmodified test compound indicates that the modified compound is a better candidate for retention in the CNS.

The ATPase activity measurement is performed using the lactate dehydrogenase/pyruvate kinase coupled enzyme system described by Tietz & Ochoa, Arch. Biochim. Biophys. Acta 78:477 (1958) to follow the decrease in absorbance at 340 nm resulting from the oxidation of NADH, which is proportional to ATPase activity. 5 mM sodium azide (NaN$_3$), 1 mM EGTA, and 0.5 mM Ouabain, each of which inhibit non-specific ATPases in the membranes, are added to the reactions to further enhance the specificity of the PgP ATPase signal. The other components in the assay mixture are 25 mM Tris, pH 7.8, 100 mM NaCl, 10 mM KCl, 5 mM MgCl$_2$, 1 mM DTT, 2 mM phosphoenolpyruvate, 1 mM NADH, 0.1 mg/ml lactate dehydrogenase, 0.1 mg/ml pyruvate kinase, 5 mM ATP, and 6 μg PgP or control membranes. For the control, as the concentration of verapamil is increased, the ATPase activity in PgP-containing membranes, but not in control membranes without verapamil, also increased. Similarly, the ATPase activity in PgP-containing membranes, but not in control membranes, may increase according to the binding or transport of the test compound by the efflux transporter.

Efflux competition assays can be performed by transfecting a tetracycline-inducible PgP expression construct (TREx-PgP) into HEK cells or other suitable cell line. The cell line optionally can be transfected with a nucleic acid encoding the transporter of interest. Cells are incubated with a PgP substrate, 5 μM calcein-AM, which passively diffuses into the cells, as well as with various concentrations of the test compound. Control cells are incubated with 5 μM calcein-AM, as well as with various concentrations of the PgP substrate verapamil. As the concentration of PgP substrate verapamil is increased, more calcein-AM accumulates in the cells and is converted to the fluorescent product calcein. Similarly, if the test compound is a PgP substrate, calcein (converted from calcein-AM) will accumulate in the cell. The accumulation of calcein is measured to determine the binding or transport of the test compound (or a modified test compound) by the efflux transporter.

Transwell monolayer efflux assays can be performed by transfecting MDCK cells with the tetracycline-inducible TREx-PgP expression vector. The cells optionally can be transfected with a nucleic acid encoding the transporter of interest. The transfected cells are seeded on polycarbonate filter membranes in transwell dishes and grown for 3-5 days, yielding a polarized monolayer with tight junctions between cells. In this example, apical to basolateral and basolateral to apical transport of 2.5 nM (approximately 100,000 cpm) radiolabeled PgP substrate $^3$H-vinblastine is measured in the absence and presence of 250 μM of the inhibitor/competitor verapamil. Apical to basolateral transport of $^3$H-vinblastine is strongly increased and basolateral to apical transport of $^3$H-vinblastine is strongly decreased in the presence of verapamil, indicating that $^3$H-vinblastine is a substrate of PgP. For a test compound (or a modified test compound) the apical to basolateral transport of, and basolateral to apical transport of, can be measured and compared to determine the binding or transport of the test compound by the efflux transporter.

Example 6

Recombinant hCAT1 Expression

An inducible CAT1 expression construct was prepared. The human CAT1 cDNA was linked to the tetracycline inducible promoter using the Gateway plasmid cloning system following manufacturer's instructions (Invitrogen). The tet-CAT1 expression construct was transfected into LLCPK-TREx cells using Fugene transfection following manufacturers instructions (Roche Biosciences). The resulting cell line was designated a LLCPK-TREx-CAT1 inducible cell line.

Example 7 hCAT1 Competition Uptake Assay

A modified competition uptake assay was developed to determine the ability of a test compound(s) to inhibit the uptake of radiolabeled substrates into LLCPK-TREx-hCAT1 cells induced to over-express hCAT1. The results are stated as affinities ($IC_{50}$).

The competition uptake assay was prepared as follows: Compounds were prepared for assay by diluting a 100 mM stock concentration (in DMSO) to the appropriate working concentration. Typically, seven-point dose response curves were prepared starting at a final assay concentration of 3 mM and carrying out three-fold dilutions. These dilutions were prepared by making a working "compound" plate that contained a 2×solution of the desired starting concentration of each test compound in duplicate in row A of a v-bottom microtiter plate. Six 3-fold serial dilutions (from row B to G) were made into the sodium free HBSS assay buffer (60 mg/L $KH_2PO_4$ (0.4 mM) (Sigma; P-0662); 0.42 g/L $KHCO_3$ (4.17 mM); (Sigma; P-6037); 1 g/L Glucose (0.5mM) (Sigma; G-7528); 2.1 g/L MOPS (10 mM) (Sigma; M-1254); 1.05 ml/L $MgCl_2.(H_2O)_6$ (Sigma; M-1028); 100 mg/L $MgSO_4.(H_2O)_7$ (Sigma; M-5921); 140 mg/L $CaCl_2$ (1.3 mM)(Sigma; C-5080); 19.1 g/L Choline Chloride (137 mM) (Sigma; C-7527), pH to 7.4 with KOH) with the appropriate amount of DMSO so that the DMSO concentration remained constant at all dilutions. The resulting "compound" plate contained serial dilutions of six compounds in duplicate. The final row (H) of the assay plate was filled with HBSS buffer alone (H1-H6) or 10 mM unlabeled Arginine in HBSS (H7-H12) to measure the total or non-specific uptake, respectively.

$^3$H-Arginine was diluted into HBSS buffer to a final concentration of 4,000 cpm/μl. Sufficient solution was prepared to allow addition of 25 μl/well (the final concentration was 100,000 cpm/well).

LLCPK-TREx-hCAT1 cells, plated in 96-well plates and treated with 2 mM butyrate and tetracycline (or tet analog (e.g., doxycycline), were removed from the $CO_2$ incubator. Growth media was removed from the cells, and the cells were washed twice in room temperature HBSS (100 μl/well/wash) using a 96-well plate washer (Bio Tek ELX405). Alternatively, cells were washed manually with equivalent volumes using a multichannel pipettor. Immediately before beginning the assay, the final 100 μl wash solution was removed from the cells by aspiration.

Using a 96-well pipettor, 25 μl from the "compound" plate was added to each well of the cell plate. The assay was started by adding 25 μl of the $^3$H-Arginine working solution. The plate was incubated at room temperature for 10 minutes. The assay was stopped by washing the cells four times with ice-cold HBSS buffer using a ELX405 plate washer (100 μl buffer/well/wash) having an angled buffer dispenser.

Scintillation fluid (200 μl) (Optiphase Supermix (Perkin Elmer) was added to each well, and the plate was covered with a 96-well adhesive plate cover and placed on a shaker for 20 minutes. The plates were counted on a 96-well plate scintillation counter for 60 sec/well. The data were analyzed using a sigmoidal dose response curve-fitting program (Prism, GraphPad, Inc, San Diego, Calif.; equation: one-site competition).

Example 8 hCAT1 Direct Uptake Assay

A modified direct uptake assay was developed to determine the ability of test compounds to be transported into LLCPK-TREx cells induced to over-express hCAT1. Four concentrations (bracketing the affinity as measured by competition assays) per compound were routinely tested. Non-specific uptake was determined by measuring the uptake into cells not induced to express the transporter ("no tet").

The direct uptake assays were prepared as follows: Compounds were prepared for assay by diluting a 100 mM stock concentration (in DMSO or water, depending on compound solubility) to the appropriate working concentration. Typically, four concentrations bracketing the $IC_{50}$ were tested. The highest test concentration for each compound was made in an Eppendorf tube and diluted into HBSS. The samples were robustly vortexed and centrifuged for 10 minutes at 13,200 rpm to spin down any precipitate. The supernatant from these samples (~150 μl/well) was carefully removed and placed into six wells of row A (cmpd 1:A1-6; cmpd 2:A7-12) or row E (cmpd 3:E1-6; cmpd 4:E7-12) of a 96-well polypropylene "compound" plate. Three additional 2-fold dilutions were made in the subsequent rows (B-D or F-G) in HBSS. With this set-up, four compounds were tested per plate: four concentrations of each compound in triplicate on cells that had either been induced (A: plus tet) or not induced (B: no tet) to express the transporter.

An internal standard of 50 μM propranolol in 50:50 ethanol:water was also prepared. To prepare standard curves, several concentrations of the test compounds were diluted into LLCPK cell extract (prepared from tet-treated, mock-incubated and extracted cells as described below) with a final internal standard concentration of 5 μM. Standards of 10, 5, 1, 0.5, 0.1, 0.05, 0.01, and 0.005 μM were routinely run for each test compound.

LLCPK-TREx-hCAT1 cells were plated in 96-well plates and treated with 2 mM butyrate and tetracycline (or a tetracycline analog; columns 1-3 and 7-9) or 2 mM butyrate without tetracycline (or a tetracycline analog; columns 4-6 and 10-12). The cells were removed from the $CO_2$ incubator, and the growth media was removed from the cells. The cells were washed twice in room temperature HBSS (100 μl/well/wash) using a 96-well plate washer (Bio Tek ELX405). Alternatively, cells were washed manually with equivalent volumes using a multichannel pipettor. Immediately before the assay was begun, the final 100 μl wash solution was removed from the cells. The assay was started by using a 96-well pipettor to add 50 μl from the "compound" plate to each well of the LLCPK-TREx-hCAT1 cell plate. The plate was incubated at room temperature for 5 minutes.

The assay was stopped by washing the cells four times with ice-cold HBSS buffer using a ELX 405 plate washer (100 μl buffer/well/wash) with an angled buffer dispenser. After the final wash, as much of the wash buffer as possible was removed by aspirating the wells with a probe that reached the bottom of the wells. (Residual salts from the wash buffer can adversely affect the LC-MS-MS by disrupting the LC method or by suppressing the MS signal.) 150 μl of a 50:50 ethanol:water solution was added to each well to lyse the cells and extract the test compound. The plate was covered and allowed to sit for 20 minutes at room temperature to ensure cell lysis. (The 50% ethanol solution is the generic solution for extraction. For compounds soluble in water or other solvents compatible with the LC-MS-MS, such solutions can be tried to determine whether they interfere with the LC-MS-MS analysis. If the organic solvent concentration is too high (>50%), it may be detrimental to the LC run).

120 μl of the cell extract was removed from each well and transferred to a fresh 96-well v-bottom polypropylene plate. This plate was covered with an adherent cover (top seal) and centrifuged for 15 minutes at 5,700 rpm (Allegra 25R centrifuge) at 4° C. to pellet any cell precipitate. 10 μl of the 50 μM propranolol solution was added to each well of a fresh 96-well plate (a plate amenable for sampling in the LC-MS-MS). 90 μl of the supernatant from the centrifuged cell extract was removed and transferred to the plate containing the 10 μl of propranolol (using a Cybi-well 96-well pipettor). The sample plate with a bubble lid suitable for use with the LC-MS-MS and placed on a plate shaker for 5 to 10 minutes to mix the sample and the propranolol. The samples were submitted for LC-MS-MS analysis. The levels of intracellular compounds were determined by converting the peak area to concentration by extrapolating from the standard curve for each compound. Uptake was expressed as μM/well.

While the uptake values in these experiments were expressed as "μM/well," the values can be easily converted to "pmol/well" or "pmol/well/unit time." All of the samples were extracted with 150 μl of extraction buffer. To convert the extrapolated "μM/well" values to "pmol/well," the following equation can be used:

$$X(10^{-6} \text{ mol/L})/\text{well} \times 150 \times 10^{-6} \text{ L} = 150 \times X \text{ pmol/well},$$

where X=the extrapolated value obtained from the standard curve.

Example 9

Arginine Competition Assay with LLCPK-TREx-CAT1 Cells

FIG. 2 depicts the results of a competition experiment using LLCPK-TREx-CAT1 cells. $^3$H-arginine was used as the substrate and unlabeled arginine, ornithine, dimethylarginine, lysine and N-methylarginine were used as competitors. The competition experiment was performed as described in Example 7. Non-specific uptake was determined by measuring the uptake into cells not induced to express the transporter ("no tet"). FIG. 2 demonstrates that in cells induced to express CAT1, the uptake of labeled arginine decreased as the concentration of unlabeled substrates increased. In control cells, uptake of labeled arginine remained at background levels and was largely unaffected by an excess of unlabeled substrates.

Example 10

Competition and Direct Uptake Assays with LLCPK-TREx-hCAT1 Cells Using Ornithine, N-Me-Arginine, and Di-Me-Arginine The competition and direct uptake assays described in Examples 7 and 8 were used to test five hCAT1 substrates: arginine, lysine, ornithine, N-Me-arginine, and di-Me-arginine. Of these five, only three, arginine, lysine, and ornithine, have $IC_{50}$ values reported in the literature (Deves et al., 1998, Transporters for Cationic Amino Acids in Animal Cells: Discovery, Structure and Function, Physiological Reviews, 78(2):487-545; Palacin et al., 1998, Molecular Biology of Mammalian Plasma Membrane Amino Acid Transporters, Physiological Reviews, 78(4):969-1054).

These five compounds, arginine, lysine, ornithine, N-Me-arginine, and di-Me-arginine, were tested in both competition and direct uptake assays. FIG. 2 shows the results of the competition assay.

Figure 3:
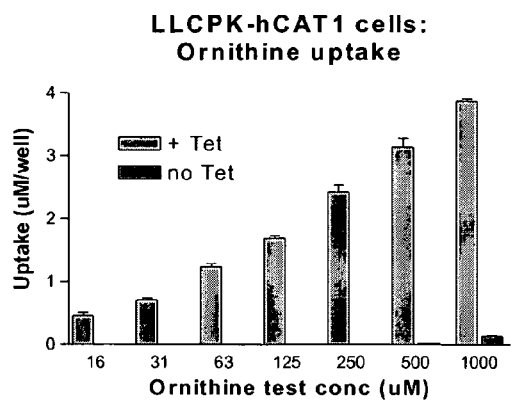
FIG. 3 shows direct uptake assays with LLCPK-TREx-CAT1 cells using ornithine, N-methyl arginine, and dimethyl arginine as substrates. (A) Dose-response (left) and specific uptake (right) of ornithine into cells induced (+TET) or un-induced (no TET) to express hCAT1. (B) Dose-response (left) and specific uptake (right) of N-methyl arginine into cells induced (+TET) or un-induced (no TET) to express hCAT1. (C) Dose-response (left) and specific uptake (right) of dimethyl arginine into cells induced (+TET) or un-induced (no TET) to express hCAT1. Specific uptake was determined by subtracting the values obtained in cells not induced to express hCAT1 from those in the induced cells and graphed vs. the test concentration of each substrate.
Figure 3:
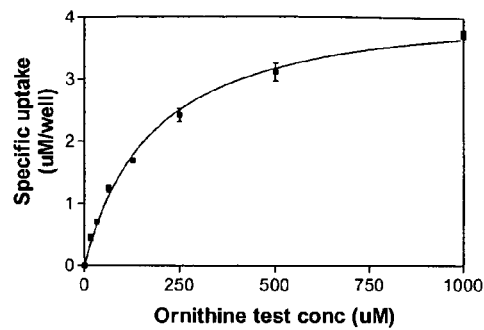
Figure 3:
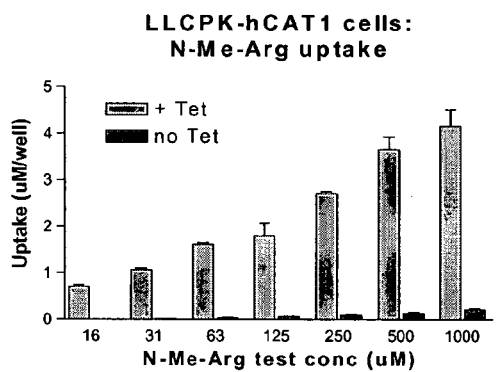
Figure 3:
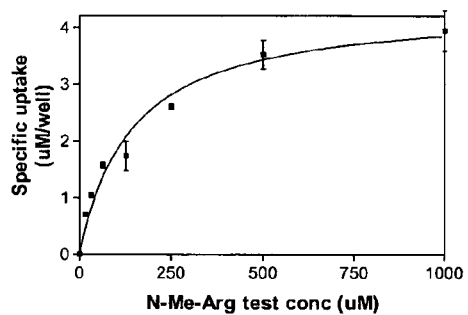
Figure 3:
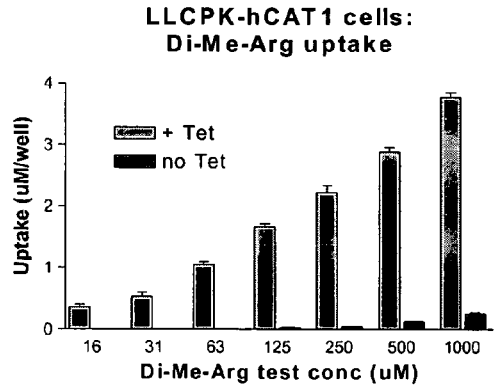
Figure 3:
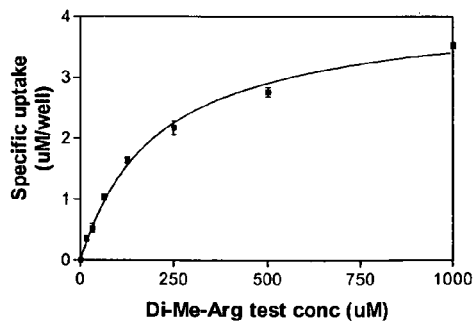

FIG. 3 shows the results of the direct uptake assays for (A) ornithine, (B) N-Me-arginine, and (C) di-Me-arginine. For each substrate, a dose-response graph (left) and specific uptake graph (right) into LLCPK-TREx-hCAT1 cells induced (+TET) or uninduced (no TET) to express hCAT1 is shown.

A summary of the results in each assay including the assay variability (% error) is shown in the Tables 5 and 6 below. The dynamic range of both the competition and direct uptake assays was well within the desired range of greater than five.

TABLE 5

Results of Competition Assays

| Competition Assay | Literature Km or $IC_{50}$ (uM) | $IC_{50}$ (μM) | $pIC_{50}$ | sem | % error |
|---|---|---|---|---|---|
| Arginine | 70-250 | 83 | 4.1 | 0.06 | 1.45 |
| Lysine | 73; 70-200 | 140 | 3.9 | 0.05 | 1.3 |
| Ornithine | 105; 70-200 | 73 | 4.1 | 0.03 | 0.8 |
| N-Me-Arg | N/A | 190 | 3.7 | 0.01 | 0.3 |
| Di-Me-Arg | N/A | 77 | 4.2 | 0.06 | 1.5 |

TABLE 6

Results of Direct Uptake Assays

| Direct Uptake Assay | Km (μM) | pKm | sem | % error | Vmax (μM/well) | sem | % error |
|---|---|---|---|---|---|---|---|
| Ornithine | 184 | 3.7 | 0.02 | 0.6 | 3.7 | 0.46 | 12.3 |
| N—Me-Arg | 158 | 3.8 | 0.04 | 1.1 | 3.9 | 0.61 | 15.7 |
| Di-Me-Arg | 177 | 3.8 | 0.05 | 1.4 | 4.5 | 0.89 | 20.0 |

Although the foregoing compounds, conjugates, and methods have been described in detail for purposes of clarity of understanding it will be obvious that certain modifications may be practiced within the scope of the claim(s) granted here from. Unless otherwise apparent from the context, any element, embodiment, or step can be used in combination with any other. All publications and patent documents cited herein are hereby incorporated by reference in their entirety for all purposes to the same extent as if each were so individually denoted.

The invention claimed is:

1. A method of screening a conjugate or conjugate moiety for capacity to be transported through the blood brain barrier, comprising:
   (a) providing a cell expressing the CAT1 transporter, wherein the CAT1 transporter is the protein encoded by SEQ ID NO:1 or has at least 90% sequence identity to the protein encoded by SEQ ID NO:1, and the CAT1 transporter can transport arginine, the CAT1 transporter being situated in the plasma membrane of the cell;
   (b) contacting the cell expressing the CAT1 transporter with a conjugate or conjugate moiety;
   (c) determining whether the conjugate or conjugate moiety passes through the plasma membrane via the CAT1 transporter, passage through the plasma membrane via the CAT1 transporter indicating the conjugate or conjugate moiety has the capacity to be transported through the blood brain barrier;
   (d) if step (b) comprises contacting the cell expressing the CAT1 transporter with a conjugate moiety and step (c) determines that the conjugate moiety passes through the plasma membrane via the CAT1 transporter, then linking the conjugate moiety to a neuropharmaceutical agent or to an imaging component to form a conjugate and repeating steps (a) through (c) with the conjugate; and
   determining that the conjugate or conjugate moiety is transported by at least one efflux transporter, wherein the at least one efflux transporter is selected from the glycoprotein (PgP) transporter, the multi-drug resistance protein (MRP1) transporter, and the breast cancer resistance protein (BCRP) transporter;
   wherein:
      the conjugate comprises a conjugate moiety linked to a neuropharmaceutical agent or to an imaging component.

2. The method of claim 1, further comprising:
   determining the CAT1 transporter activity of the conjugate or conjugate moiety;
   determining the efflux transporter activity of the conjugate or conjugate moiety;
   modifying the conjugate or conjugate moiety; determining the CAT1 transporter activity of the modified conjugate or modified conjugate moiety;
   determining the efflux transporter activity of the modified conjugate or modified conjugate moiety; and
   comparing the ratio of the CAT1 transporter activity to the efflux transporter activity for the conjugate or conjugate moiety and the ratio of the CAT1 transporter activity to the efflux transporter activity for the modified conjugate or modified conjugate moiety wherein an increased ratio of CAT1 transporter activity to efflux transporter activity for the modified conjugate or modified conjugate moiety demonstrates that the modification improves the capacity of the conjugate or conjugate moiety to be transported through the blood brain barrier.

3. The method of claim 2, wherein the efflux transporter activity is determined by conducting an assay selected from the group consisting of:
   (a) an efflux transporter ATPase activity assay;
   (b) an efflux transporter competition assay; and
   (c) a direct efflux transport assay across a polarized monolayer of cells.

4. The method of claim 2, wherein the efflux transporter activity is the $V_{max}$ for the efflux transporter, and the CAT1 transporter activity is the $V_{max}$ for the CAT1 transporter.

5. A method of screening an agent or imaging component for decreased side effects in the central nervous system (CNS), comprising:
   (a) providing
      (i) an agent having a pharmacological activity, wherein the pharmacological activity is useful for treating a disease present in a tissue other than the CNS, and the agent causes undesired side effects in the CNS if the agent enters the CNS; or
      (ii) an imaging component useful for imaging a tissue other than the CNS, and the imaging component causes undesired side effects in the CNS if the imaging component enters the CNS, wherein the imaging component is selected from the group consisting of a fluorophore, a chromophore, and a paramagnetic component;

(b) providing a cell expressing at least one CAT1 transporter that transports substrates across the blood brain barrier; wherein the CAT1 transporter is the protein encoded by SEQ ID NO:1 or has at least 90% sequence identity to the protein encoded by SEQ ID NO:1, and the CAT1 transporter can transport arginine;
(c) contacting the cell with the agent or imaging component;
(d) determining that the agent or imaging component is a substrate for the CAT1 transporter;
(e) modifying the agent or imaging component;
(f) contacting the cell with the modified agent or modified imaging component; and
(g) determining whether the modified agent or modified imaging component passes through the plasma membrane via the CAT1 transporter with a lower $V_{max}$ than the agent or imaging component, a lower $V_{max}$ for the modified agent or modified imaging component indicating that the modification decreases the capacity of the modified agent or modified imaging component relative to the agent or imaging component to cross the blood brain barrier, thereby decreasing undesired side effects in the CNS.

6. The method of claim 5, wherein the cell is transformed or injected with a nucleic acid encoding the CAT1 transporter or the cell is a brain microvessel endothelial cell.

7. The method of claim 5, wherein the modifying comprises linking the agent or imaging component to a conjugate moiety to form a conjugate.

8. The method of claim 7, wherein the conjugate moiety is an inhibitor of the CAT1 transporter or is a substrate for the efflux transporter.

* * * * *

SEQUENCE LISTING

<160> NUMBER OF SEQ ID NOS: 7

<210> SEQ ID NO 1
<211> LENGTH: 7248
<212> TYPE: DNA
<213> ORGANISM: Homo sapiens

<400> SEQUENCE: 1

```
gcggccgcgg gctcccgcta accgcagcct ccactcctct ccccgcgcgc cgcgccccg      60 ccccgccccg cccggtctcg ccggccgagc gtccgttggt ccttgagcgc gtccgacagt     120
ctgtctgttc gcgatcctgc cggagccccg ccgccgccgg cttggattct gaaaccttcc     180
ttgtatccct cctgagacat ctttgctgca agatcgaggc tgtcctctgg tgagaaggtg     240
gtgaggcttc ccgtcatatt ccagctctga acagcaacat ggggtgcaaa gtcctgctca     300
acattgggca gcagatgctg cggcggaagg tggtggactg tagccgggag gagacgcggc     360
tgtctcgctg cctgaacact tttgatctgg tggccctcgg ggtgggcagc acactgggtg     420
ctggtgtcta cgtcctggct ggagctgtgg cccgtgagaa tgcaggccct gccattgtca     480
tctccttcct gatcgctgcg ctggcctcag tgctggctgg cctgtgctat ggcgagtttg     540
gtgctcgggt ccccaagacg ggctcagctt acctctacag ctatgtcacc gttggagagc     600
tctgggcctt catcaccggc tggaacttaa tcctctccta catcatcggt acttcaagcg     660
tagcgagggc ctggagcgcc accttcgacg agctgatagg cagacccatc ggggagttct     720
cacggacaca catgactctg aacgcccccg gcgtgctggc tgaaaacccc gacatattcg     780
cagtgatcat aattctcatc ttgacaggac ttttaactct tggtgtgaaa gagtcggcca     840
tggtcaacaa aatattcact tgtattaacg tcctggtcct gggcttcata atggtgtcag     900
gatttgtgaa aggatcggtt aaaaactggc agctcacgga ggaggatttt gggaacacat     960
caggccgtct ctgtttgaac aatgacacaa aagaagggaa gcccggtgtt ggtggattca    1020
tgcccttcgg gttctctggt gtcctgtcgg gggcagcgac ttgcttctat gccttcgtgg    1080
gctttgactg catcgccacc acaggtgaag aggtgaagaa cccacagaag gccatcccg     1140 tggggatcgt ggcgtccctc ttgatctgct tcatcgccta ctttggggtg tcggctgccc    1200
tcacgctcat gatgcccta ttctgcctgg acaataacag ccccctgccc gacgccttta    1260
agcacgtggg ctgggaaggt gccaagtacg cagtggccgt gggctccctc tgcgctcttt    1320
ccgccagtct tctaggttcc atgtttccca tgcctcgggt tatctatgcc atggctgagg    1380
atggactgct atttaaattc ttagccaacg tcaatgatag gaccaaaaca ccaataatcg    1440
ccacattagc ctcgggtgcc gttgctgctg tgatggcctt cctctttgac ctgaaggact    1500
tggtggacct catgtccatt ggcactctcc tggcttactc gttggtggct gcctgtgtgt    1560
```

```
tggtcttacg gtaccagcca gagcagccta acctggtata ccagatggcc agtacttccg   1620
acgagttaga tccagcagac caaaatgaat tggcaagcac caatgattcc cagctggggt   1680
ttttaccaga ggcagagatg ttctctttga aaaccatact ctcacccaaa acatggagc    1740 cttccaaaat ctctgggcta attgtgaaca tttcaaccag ccttatagct gttctcatca   1800
tcaccttctg cattgtgacc gtgcttggaa gggaggctct caccaaaggg gcgctgtggg   1860
cagtcttcct gctcgcaggg tctgccctcc tctgtgccgt ggtcacgggc gtcatctgga   1920
ggcagcccga gagcaagacc aagctctcat ttaaggttcc cttcctgcca gtgctcccca   1980
tcctgagcat cttcgtgaac gtctatctca tgatgcagct ggaccagggc acctgggtcc   2040
ggtttgctgt gtggatgctg ataggcttca tcatctactt tggctatggc ctgtggcaca   2100
gcgaggaggc gtccctggat gccgaccaag caaggactcc tgacggcaac ttggaccagt   2160
gcaagtgacg cacagccccg cccccggag gtggcagcag cccgaggga cgccccaga     2220 ggaccgggag gcaccccacc ctccccacca gtgcaacaga aaccacctgc gtccacaccc   2280
tcactgcagc caaaggtgca attacttgac ctgcagcccc agcccaccct cggctctgca   2340
gccggttctc cgggccctgg tcacctccag acagctgcct ggccggggcc actaggctgc   2400
ggctggccac tgtgtctcct cacttctctg aacaaagcag ttcctcccct accagctcag   2460
ccccgagctg ccgcagcctc aggcagaacg gaggtcacct tctctcctta tcttgggaac   2520
caggccttcc tcccggggac tgttctggga ttgaaattgt gcatactcca aactttcgca   2580
gccatcttcc cgctcagccc cagacaccca gcaatcaagc cagatgagta ccacaaaaca   2640
gtgtgtcccc agcagctccc cacccccagag ccaaatgaca gtagtgcact taaaaaggaa   2700
aatcaggcct gttgtccttc tccggttgca ttcagatggg tcattagggc cggaccctgc   2760
ctgccccttg gcttctcagg gctttgctct gacaccatga cagctgcccg gggctgaggg   2820
cagctggctc cactcaaatg aggaagaagg gatcactccc attagggcct gctttgctta   2880
tgcatgtgtg tgcacatgca tgtaaaccag ggaccttcag ctcacggcct ccaggcctgg   2940
gccagttctt gctgctcctg ccgtctcccc cgactggctg tgtcctgagt aactggaaca   3000
tgagacagta tctgcaggac tggccccatg gtggccgagt cagaagtctg tttcctgtga   3060
gtcgccaccg ttcactcagt cttgccctcc catgctttgg agccagtctg gtggctcctg   3120
taaggttctc aaggctggtg gcagctcagt ctggggtcag gacatgtcgg ggtcatgcgt   3180
ttctggccct gacataagct gtctggcctc tctgtgacat gatgaaattg aaatcaatcc   3240
acagtccatg aaattgtgac actccaccag attaagttag ggcataacat taacttggaa   3300
atggccatgt catcacccct gcggctgtcc tatagctgag atgcgtgggt cgcaggggag   3360
gtgatttcta ggcatattgc tgtcccttt gtgtatctgt catccggatg cttcggaccc   3420
cacgcctctg caagtgggag agacccgagc atcctcccca cccccatagc tccagtgcac   3480
gccacccccg tcttgcctgg gtcggggcct gcggccagca ccatttcaca cacactcctt   3540
gtagatggga gccagaggaa acctgaacgt gggtggagcg ttccactgag tctacttcag   3600
gagacagaag gcccatgctg atgggggagg aggaggggacg tgggcatttt ggacaccagg   3660
ggaaatggaa atgctgcttt caaaacttag tttcctttcc atttcttcct agtctggcct   3720
ttgacacaaa tctggtagaa agaagcctga taaattgagg gcacttgtac cctccctgtg   3780 ccccagaag gttcttggag agaagtgcaa gaatttgtga acacggcggt ggagggcggg   3840
tggatggcca tgggctgggc ctccgtatca ggcctgctca ccttgctggg agctttattc   3900
tgatctcatt ttgaatgttc cagagggagc atcataagag cccagagctc cgatttccaa   3960
```

```
agagtgatat tgacatttat ggagattggt gttgtaacat attttgataa atactaactt    4020
attttgttgg ggttttggtt gtctcttgtc ttaggacctg gtagttattt gcttgatttt    4080
tttttccgtt attttctaca taggcaaaga gaattcgagg gatagacagt ctccaagaaa    4140
agtgaagtgg tgggagagaa ttgctttttt ctttttttc ttttctctag ttttctttc      4200 tggctgagat ttccgtgcaa gacagcaccc aatagactat ttagagttga catttgacat    4260
tttaatgggc gccatggctc attttgtaga ttgagaaggt gcgtctcccc tgctccaagt    4320
ctcatcatga cagcgtgctg acagctggga gtctgtggcc ttcctcacgc agaggcctta    4380
aagctggaca cagaagcacg cctaggctgg gcagggatgg gacccatgcc ccctccttag    4440
aggacgggct tcctggttag gaaaggacac gtggggggtgc cttgcataat agttcactgg   4500
tcaccgtgct tttatgagta gtgttttgt gcacttgcca ggggttttct ctctgtgtga     4560
gaggggagtg atttaagcaa tggtgtctgg agtaagcctt acaattttaa tagacttttt    4620
cttatcatat ccctcatttc tttccctgaa ataaaaatac acacaagcaa aaaaaaatg     4680 atagtttcac atctcttagt tcccttgccc aaacaagaat attcttagtt ccactggcca    4740
ggattttcct acatagtcag aacttacaca ttactagagg cacacccacc aaggagtatt    4800
gtgtctactt ttatctgtgc accagccaca aatacccaca ttggaaagac ccatttgtga    4860
tgggtaaaca tcccttcctg tctcccacaa cccctgtgac tgccctgcat gtgttcatga    4920
cctccgaagg cccaaattca tgaagcagca aacccagcag atctccaccc ccctgcctca    4980
ggacctctgc tgaagagggg gatgaagtgg gtctccaggg aggcagtggg ggccttgttg    5040
gcagctggct cggagccgg cttacaggag ggcagctctg cagttgggag gggcaccgtc     5100
cggaggagac caggcctcta cacaccccc actctactta tcatccctgc tcacacaccc    5160
ttgtccaagg ctttatgcat cggattatt tttccaaatc aagaggacag tgatagatgc     5220
attttcccca ggctgtctca gaaaggtcgc taaatgtata ctgttgtcag aattgctgag    5280
atctcccccc acttttggtt tttgcagcag taaaaactct ttccactgtg acttatttc     5340 tctctcaggc agccagccac ctggtccctt gtgctgactc tagcacagtg gccaggatcc    5400
aatacgagtc caggggtgac cgcaggatgg tgggggcagc gggcttctcc acctaccca    5460 gccaccaagg ccctgacgca ctgcctcctg caccttcagc acatccctgt gcacagctgg    5520
aagggtgcat ggcccgctca ccttttgttca gatgggtgga aacgctgatg ataccagctc   5580
ctccctgccg tgcccctgcc acggagcagg cattgtgaac tggctggtgt ttgcagtccc    5640
acgtggcatg gcctccagcc caacccacag tggagactgg agacagggca atgagtctgg    5700 tcggggcac gtggacatgc cccataggg ccccacccag acttaacagg caaggtcctg      5760
ggcattgcgc gacgcaggac tcaatgctaa agcaagcctg cctggctctg tgccagggcc    5820
cctcttctga tttacacatc ccatttttac acagacccctt ccttcttaat aaaggctgac   5880
agttctgttg gcagccaaga acccacacca tgaagacagg gagtgagggg cctttgtgcc    5940
caactccagc acagctgcgt tctgggtgt gtgagaggca tgttcgtgtc tgtgcgctgg     6000
tggtctcgtg agacagttcc gaggacgggg aaattgcagg gtggtggggg cgtgaggctt    6060
atatgtggaa ctgatgcaga gttcgcctgc agacggatct ggatatacac tatgtataat    6120
tgttacgtgt aatttaaaat atatctgttt gccatcgtca tgagaagatt atatgtaagg    6180
ctctgaaggg agagggagat gtacattctg ccaggctcct ggggacctta tccgagtcat    6240
gaaattgatg actgttgatc cagtggtgca agaagctaca ctccatgtgt catcacgctt    6300
```

```
atgactccta atgtattttt aaggcaaaaa atgtcagccg actccatctt caccoctcga    6360 ttcctcgagt ccagcctttc tgtgccagtg cttcactgag ccacaacgct ctcgccatcg    6420
ggacccggct gggcctggag tctcggggca cagttgccat ggagccctcc tgggtcattc    6480
tacaaatgtg ctgagtgcca gctgaaaacc ccacaggaga tggagtacct tggccaagct    6540
taaagagaag attttctcag ggtatttatt agtgtgtcca gcagggtcag gaagcaggat    6600
ggaaagatgc attcagactg ttaatttatt aacaaggcaa atgattttgt gtttcttgat    6660
gacagactat taagtttggg acttattttc ccatttgaga agttataata tatatttaag    6720
atgataagtt tcctgcttaa gttgtgcctt tcagcttcaa tgagtttaag gagcactaag    6780
ggtaatgata ccaatgaggg ttggtttatt atcaaacctg aatagctgtg gtttctccag    6840
taaatatttt cttctactga acatggagcc attattaaga gttgtgtgtt ttttattatg    6900
tacatttgta tattttttg cttgtttgat gttctatttt tctaatagtt ttcttttagt    6960
ttcttaaagt tgtgatacta gatttagatt ctgatgctaa ctgcaaatca ggttggtctc    7020
tgctgggtct ctcctgcttt tattttactt taaggacaag tgtagttgtc gtccaccacc    7080
tttcaaaaaa tgtgaaactg ccctgcctcc ccttttgct gacaacactg tgtacattga     7140
ccacttccta ccatacttta tgttgtaaaa tcaaactctt ttgtggtaca ttatctcatg    7200
cttctgcaaa ttcgaataaa ttctatggct tccaaaaaaa aaaaaaaa                 7248
```

<210> SEQ ID NO 2
<211> LENGTH: 26
<212> TYPE: DNA
<213> ORGANISM: Artificial
<220> FEATURE:
<223> OTHER INFORMATION: CAT1 mRNA forward primer

<400> SEQUENCE: 2
tggcactctc ctggcttact cgttgg                                         26

<210> SEQ ID NO 3
<211> LENGTH: 26
<212> TYPE: DNA
<213> ORGANISM: Artificial
<220> FEATURE:
<223> OTHER INFORMATION: CAT1 mRNA reverse primer

<400> SEQUENCE: 3
ctcgtcggaa gtactggcca tctggt                                         26

<210> SEQ ID NO 4
<211> LENGTH: 26
<212> TYPE: DNA
<213> ORGANISM: Artificial
<220> FEATURE:
<223> OTHER INFORMATION: GLUT1 mRNA forward primer

<400> SEQUENCE: 4
ggggcatgat tggctccttc tctgtg                                         26

<210> SEQ ID NO 5
<211> LENGTH: 26
<212> TYPE: DNA
<213> ORGANISM: Artificial
<220> FEATURE:
<223> OTHER INFORMATION: GLUT1 mRNA reverse primer

<400> SEQUENCE: 5
aggccgcagt acacaccgat gatgaa                                         26

-continued

```
<210> SEQ ID NO 6
<211> LENGTH: 26
<212> TYPE: DNA
<213> ORGANISM: Artificial
<220> FEATURE:
<223> OTHER INFORMATION: BNP1 mRNA forward primer

<400> SEQUENCE: 6 cacccccgc tttcctttat ctccag                                          26

<210> SEQ ID NO 7
<211> LENGTH: 26
<212> TYPE: DNA
<213> ORGANISM: Artificial
<220> FEATURE:
<223> OTHER INFORMATION: BNP1 mRNA reverse primer

<400> SEQUENCE: 7
ctgctggtag gggagatgtg aagtgg                                         26
```